(12) United States Patent
Barta et al.

(10) Patent No.: US 10,307,433 B2
(45) Date of Patent: *Jun. 4, 2019

(54) COMPOSITION AND METHODS OF USE OF SMALL MOLECULES AS BINDING LIGANDS FOR THE MODULATION OF PROPROTEIN CONVERTASE SUBTILISIN/KEXIN TYPE 9(PCSK9) PROTEIN ACTIVITY

(71) Applicant: SRX CARDIO, LLC, Pittsford, NY (US)

(72) Inventors: Thomas E. Barta, Carrboro, NC (US); Jonathan W. Bourne, Fairport, NY (US); Kyle D. Monroe, Pittsford, NY (US); Michael M. Muehlemann, Liverpool, NY (US)

(73) Assignee: SRX Cardio, LLC, Pittsford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/989,360

(22) Filed: May 25, 2018

(65) Prior Publication Data

US 2018/0303855 A1     Oct. 25, 2018

Related U.S. Application Data

(63) Continuation of application No. 15/505,017, filed as application No. PCT/US2015/046145 on Aug. 20, 2015, now Pat. No. 10,034,892.

(60) Provisional application No. 62/133,093, filed on Mar. 13, 2015, provisional application No. 62/040,264, filed on Aug. 21, 2014.

(51) Int. Cl.
| | |
|---|---|
| *A61K 31/675* | (2006.01) |
| *C07F 9/59* | (2006.01) |
| *C07F 9/6518* | (2006.01) |
| *A61K 45/06* | (2006.01) |
| *A61K 31/41* | (2006.01) |
| *A61K 31/454* | (2006.01) |
| *A61K 31/4245* | (2006.01) |
| *A61K 31/683* | (2006.01) |
| *A61K 38/00* | (2006.01) |
| *A61K 38/05* | (2006.01) |
| *C07D 401/12* | (2006.01) |
| *C07D 403/12* | (2006.01) |
| *C07D 413/14* | (2006.01) |
| *C07F 9/653* | (2006.01) |
| *C07K 5/065* | (2006.01) |

(52) U.S. Cl.
CPC ............ *A61K 31/675* (2013.01); *A61K 31/41* (2013.01); *A61K 31/4245* (2013.01); *A61K 31/454* (2013.01); *A61K 31/683* (2013.01); *A61K 38/005* (2013.01); *A61K 38/05* (2013.01); *A61K 45/06* (2013.01); *C07D 401/12* (2013.01); *C07D 403/12* (2013.01); *C07D 413/14* (2013.01); *C07F 9/59* (2013.01); *C07F 9/6518* (2013.01); *C07F 9/65312* (2013.01); *C07K 5/06078* (2013.01)

(58) Field of Classification Search
CPC ..................................................... A61K 31/675
USPC ......................................................... 544/358
See application file for complete search history.

(56) References Cited

U.S. PATENT DOCUMENTS

| | | | |
|---|---|---|---|
| 8,518,912 B2 | 8/2013 | Caroff et al. | 514/86 |
| 8,883,157 B1 | 11/2014 | Clube | 424/146.1 |
| 2009/0264315 A1 | 10/2009 | Burgess | 506/15 |
| 2010/0324024 A1 | 12/2010 | Kuduk et al. | 514/215 |
| 2012/0252796 A1 | 10/2012 | Pingali et al. | 514/227.8 |
| 2013/0184284 A1 | 7/2013 | Ewing et al. | 514/252.03 |
| 2014/0322355 A1 | 10/2014 | Oslob et al. | 424/649 |

FOREIGN PATENT DOCUMENTS

| | | |
|---|---|---|
| EP | 1210581 | 6/2002 |
| WO | WO 2009039466 | 3/2009 |
| WO | WO 2009076372 | 6/2009 |
| WO | WO 2013158300 | 10/2013 |
| WO | WO 2014127316 | 8/2014 |

OTHER PUBLICATIONS

Abifadel, et al., "Mutations in PCSK9 Cause Autosomal Dominant Hypercholesterolemia." *Nat Genet*, 34(2):154-156 (2003).
Anonomyous, "Bristol-Myers Squibb Selects Isis Drug Targeting PCSK9 as Development Candidate for Prevention and Treatment of Cardiovascular D." *Press Release. FierceBiotech. Apr. 8, 2008.* (2008).
Benjannet, et al., "Effects of the Prosegment and Ph on the Activity of PCSK9: Evidence for Additional Processing Events." *J Biol Chem*, 285(52):40965-40978 (2010).
Berge, et al., "Pharmaceutical Salts." *J Pharm Sci*, 66(1):1-19 (1977).
Bhatnagar, et al., "Hypercholesterolaemia and Its Management." *BMJ*, 337:a993 (2008).

(Continued)

*Primary Examiner* — Taofiq A Solola
(74) *Attorney, Agent, or Firm* — Medlen & Carroll, LLP

(57) ABSTRACT

This invention is related to the field of PCSK9 biology and the composition and methods of use of small molecule ligands for modulation of PCSK9 biological activity. In particular, the invention provides compositions of small molecule compounds that modulate circulating levels of low density lipoproteins by altering the conformation of the protein PCSK9. Binding these small molecule ligands to PCSK9 alters the conformation of the protein, modifying the interaction between PCSK9 and an endogenous low density lipoprotein receptor, and can lead to reduced or increased levels of circulating LDL-cholesterol. High LDL cholesterol levels are associated with increased risk for heart disease. Low LDL-cholesterol levels may be problematic in other conditions, such as liver dysfunction; thus, there is also utility for small molecule ligands that can raise LDL levels.

20 Claims, 4 Drawing Sheets
Specification includes a Sequence Listing.

(56) References Cited

OTHER PUBLICATIONS

Biggerstaff and Wooten, "Understanding Lipoproteins as Transporters of Cholesterol and Other Lipids." *Adv Physiol Educ*, 28(1-4):105-106 (2004).
Carmena, et al., "Atherogenic Lipoprotein Particles in Atherosclerosis." *Circulation*, 109(23 Suppl 1):III2-7 (2004).
Citkowitz, et al., "Polygenic Hypercholesterolemia". *eMedicine Medscape*, emedicine.medscape.com/article/121424-overview. (2010).
DeVay, et al., "Characterization of Proprotein Convertase Subtilisin/Kexin Type 9 (PCSK9) Trafficking Reveals a Novel Lysosomal Targeting Mechanism Via Amyloid Precursor-Like Protein 2 (Aplp2)." *J Biol Chem*, 288(15):10805-10818 (2013).
Finn, et al., "Concept of Vulnerable/Unstable Plaque." *Arterioscler Thromb Vasc Biol*, 30(7):1282-1292 (2010).
Frank-Kamenetsky, et al., "Therapeutic RNAi Targeting PCSK9 Acutely Lowers Plasma Cholesterol in Rodents and LDL Cholesterol in Nonhuman Primates." *Proc Natl Acad Sci U S A*, 105(33):11915-11920 (2008).
Goldstein, et al., "Receptor-Mediated Endocytosis: Concepts Emerging from the LDL Receptor System." *Annu Rev Cell Biol*, 1:1-39 (1985).
Graham, et al., "Antisense Inhibition of Proprotein Convertase Subtilisin/Kexin Type 9 Reduces Serum LDL in Hyperlipidernic Mice." *J Lipid Res*, 48(4):763-767 (2007).
Grundy, et al., "Primary Prevention of Coronary Heart Disease: Guidance from Framingham: A Statement for Healthcare Professionals from the AHA Task Force on Risk Reduction. American Heart Association." *Circulation*, 97(18):1876-1887 (1998).
Gupta, et al., "A Locked Nucleic Acid Antisense Oligonucleotide (LNA) Silences PCSK9 and Enhances LDLR Expression in Vitro and in Vivo." *PLoS One*, 5(5):e10682 (2010).
Hobbs, et al., "The LDL Receptor Locus in Familial Hypercholesterolemia: Mutational Analysis of a Membrane Protein." *Annu Rev Genet*, 24:133-170 (1990A).
Hobbs, et al., "The LDL Receptor Locus in Familial Hypercholesterolemia: Mutational Analysis of a Membrane Protein." *Annu Rev Genet*, 24:133-170 (1990B).
Innerarity, et al., "Familial Defective Apolipoprotein B-100: A Mutation of Apolipoprotein B That Causes Hypercholesterolemia." *J Lipid Res*, 31(8):1337-1349 (1990).
Jacobs, et al., "Report of the Conference on Low Blood Cholesterol: Mortality Associations." *Circulation*, 86(3):1046-1060 (1992).
Kontush and Chapman, "Antiatherogenic Small, Dense HDL—Guardian Angel of the Arterial Wall?". *Nat Clin Pract Cardiovasc Med*, 3(3):144-153 (2006).
Lambert, et al., "The Pcsk9 Decade." *J Lipid Res*, 53(12):2515-2524 (2012).
Lewington, et al., "Blood Cholesterol and Vascular Mortality by Age, Sex, and Blood Pressure: A Meta-Analysis of Individual Data from 61 Prospective Studies with 55,000 Vascular Deaths." *Lancet*, 370(9602):1829-1839 (2007).
Lindholm, et al., "PCSK9 LNA Antisense Oligonucleotides Induce Sustained Reduction of LDL Cholesterol in Nonhuman Primates." *Mol Ther*, 20(2):376-381 (2012).
Lopez, "Inhibition of PCSK9 as a Novel Strategy for the Treatment of Hypercholesterolemia." *Drug News Perspect*, 21(6):323-330 (2008).
Mä, et al., "Accumulation of "Small Dense" Low Density Lipoproteins (LDL) in a Homozygous Patients with Familial Defective Apolipoprotien B-100 Results from Heterogenous Interaction of Ldl Subfractions with the LDL Receptor." *Journal of Clinical Investigation*, 92(6):2922-2933 (1993).
Mayer, et al., "Annexin A2 Is a C-Terminal PCSK9-Binding Protein That Regulates Endogenous Low Density Lipoprotein Receptor Levels." *J Biol Chem*, 283(46):31791-31801 (2008).
Seidah, et al., "The Secretory Proprotein Convertase Neural Apoptosis-Regulated Convertase 1 (Narc-1): Liver Regeneration and Neuronal Differentiation." *Proc Natl Acad Sci U S A*, 100(3):928-933 (2003).
Shan, et al., "Pcsk9 Binds to Multiple Receptors and Can Be Functionally Inhibited by an EGF-a Peptide." *Biochem Biophys Res Commun*, 375(1):69-73 (2008).
Shan, et al., "PCSK9 Binds to Multiple Receptors and Can Be Functionally Inhibited by an EGF-a Peptide." *Biochem Biophys Res Comm*, 375(1):69-73 (2008).
Steinberg and Witztum "Inhibition of PCSK9: A Powerful Weapon for Achieving Ideal LDL Cholesterol Levels." *Proc Natl Acad Sci USA*, 106(24):9546-9547 (2009).
Suarez, "Relations of Trait Depression and Anxiety to Low Lipid and Lipoprotein Concentrations in Healthy Young Adult Women." *Psychosom Med*, 61(3):273-279 (1999).
Taylor, et al., "Statins for the Primary Prevention of Cardiovascular Disease." *Cochrane Database Syst Rev*(1):CD004816 (2011).
Zhang, et al., "Identification of a Small Peptide That Inhibits PCSK9 Protein Binding to the Low Density Lipoprotein Receptor." *J Biol Chem*, 289(2):942-955 (2014).
Schroeder, et al., "Design and Synthesis of Truncated EGF-A Peptides that Restore LDL-R Recycling in the Presence of PCSK9 In Vitro", Chemistry & Biology, vol. 21, pp. 284-294, (2014).

US 10,307,433 B2

COMPOSITION AND METHODS OF USE OF SMALL MOLECULES AS BINDING LIGANDS FOR THE MODULATION OF PROPROTEIN CONVERTASE SUBTILISIN/KEXIN TYPE 9(PCSK9) PROTEIN ACTIVITY

FIELD OF INVENTION

This invention is related to the field of PCSK9 biology. In particular, the invention provides compositions and methods of use of small molecule ligands that bind with the PCSK9 protein, and differentially modify PCSK9 biological activity in cells. These changes may include alteration in PCSK9 binding to, or dissociating from, LDLR, changes in LDLR number on the cell surface, or changes in the rate of LDL internalization.

BACKGROUND

Elevated plasma levels of low density lipoprotein cholesterol (LDL-C) represent the greatest risk factor for the development of coronary heart disease. Clearance of LDL-C from the plasma occurs primarily by the liver through the action of LDL receptors (LDLRs), which are cell surface glycoproteins that bind to apolipoprotein B100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein (LDL) receptor (LDLR) mediates efficient endocytosis of VLDL, VLDL remnants, and LDL. As part of the endocytic process, the LDLR releases lipoproteins into hepatic endosomes.

One approach to modulating LDL-cholesterol levels would be to identify small compound ligands which bind to PCSK9 and alter the kinetics of the interaction between PCSK9 and the LDLR such that the rate of lipoprotein clearance by LDLR endocytosis is increased or decreased, as desired.

SUMMARY OF THE INVENTION

This invention is related to the field of PCSK9 biology and treatment of hypercholesterolemia and hypocholesterolemia. In particular, the invention provides compositions of ligands that bind and alter PCSK9 biological conformation and methods that use these ligands to modify PCSK9 activity to change circulating levels of low density lipoprotein in the blood. These ligands may be small molecule ligands, and are small chemical compounds, and more preferably small molecule compounds less than 600 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

In one embodiment, the present invention contemplates a method, comprising: a) providing; i) a PCSK9 protein, wherein said protein comprises a binding site that induces allosteric modulation and a low density lipoprotein receptor binding site; ii) a small molecule compound capable of binding said binding site iii) a plurality of hepatocyte cells comprising a low density lipoprotein receptor and low density lipoproteins; b) binding said small molecule compound to said binding site, wherein said small molecule compound induces a conformational shift of said protein; and c) modulating the affinity of said low density lipoprotein receptor binding site for said low density lipoprotein receptor by said conformational shift. In one embodiment, the small molecule compound is selected from the group consisting of SRX75, SRX76, SRX204, SRX200, SRX201, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225. In one embodiment, the small molecule compound is of the formula:

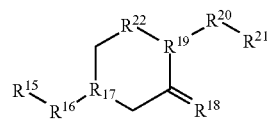

wherein: i) $R^{15}$ is selected from the group consisting of H, alkyl, cyclic alkyl, branched alkyl, and substituted alkyl; ii) $R^{16}$ is selected from the group consisting of nothing and NH; iii) $R^{17}$ is selected from the group consisting of N and CH; iv) $R^{18}$ is selected from the group consisting of $H_2$ and O; v) $R^{19}$ is selected from the group consisting of C and N; vi) $R^{20}$ is selected from the group consisting of nothing, $CH_2$, O, and NH; vii) $R^{21}$ is selected from the group consisting of aryl, substituted aryl, 5 or 6 membered aromatic heterocycle$_{[O]}$ that is substituted or unsubstituted, cyclic alkyl, 5 or 6 membered non-aromatic heterocycle, and branched alkyl; and viii) $R^{22}$ is $CH_2$ or nothing.

In one embodiment, the small molecule compound is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the conformational shift of said protein is selected from the group consisting of an induced fit shift and a biomechanical shift. In one embodiment the small molecule compound is an organic chemical compound. In one embodiment the small molecule compound is an organic chemical compound less than 800 Da. In one embodiment the small molecule compound is an organic chemical compound greater than 100 Da and less than 800 Da. In one embodiment the small molecule compound is an organic chemical compound greater than 100 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group consisting of SRX75, SRX76, SRX204, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the present invention contemplates, a method, comprising: a) providing; i) a PCSK9 protein, wherein said protein comprises a binding site that induces allosteric modulation and a low density lipoprotein receptor binding site; ii) a small molecule ligand capable of binding said binding site; iii) a plurality of hepatocyte cells comprising a population of low density lipoprotein receptors; b) binding said small molecule ligand to said binding site, wherein said small molecule ligand induces a conformational shift of said protein; c) modulating said population of said low density lipoprotein receptors by said conformational shift. In one embodiment, the small molecule ligand is selected from the group consisting of SRX75, SRX76, SRX204, SRX200, SRX201, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225. In one embodiment, the small molecule compound is of the formula:

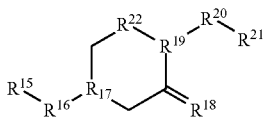

wherein: i) $R^{15}$ is selected from the group consisting of H, alkyl, cyclic alkyl, branched alkyl, substituted alkyl; ii) $R^{16}$ is selected from the group consisting of nothing, and NH; iii) $R^{17}$ is selected from the group consisting of N, and CH; iv) $R^{18}$ is selected from the group consisting of $H_2$, and O; v) $R^{19}$ is selected from the group consisting of C, and N; vi) $R^{20}$ is selected from the group consisting of nothing, $CH_2$, O, and NH; vii) $R^{21}$ is selected from the group consisting of aryl, substituted aryl, 5 or 6 membered aromatic heterocycle$_{[O]}$ that is substituted or unsubstituted, cyclic alkyl, 5 or 6 membered non-aromatic heterocycle, and branched alkyl; viii) $R^{22}$ is $CH_2$ or nothing.

In one embodiment, the small molecule ligand is an allosteric inhibitor ligand wherein said modulating increases said population of said low density lipoprotein receptors measurable on the cell surface of said plurality of hepatocytes. In one embodiment, the conformational shift of said protein is selected from the group consisting of an induced fit shift and a biomechanical shift. In one embodiment the small molecule compound is an organic chemical compound. In one embodiment the small molecule compound is an organic chemical compound less than 800 Da. In one embodiment the small molecule compound is an organic chemical compound greater than 100 Da and less than 800 Da. In one embodiment the small molecule compound is an organic chemical compound greater than 100 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group consisting of SRX75, SRX76, SRX204, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the ligand is selected from the group consisting of: SRX75, SRX76, SRX200, SRX201, SRX204, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the present invention contemplates a compound including, but not limited to, SRX75, SRX76, SRX200, SRX201, SRX204, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the compound is formulated as a pharmaceutical composition. In one embodiment, the pharmaceutical composition further comprises a pharmaceutical drug. In one embodiment, the pharmaceutical drug is selected from the group consisting of a statin, a cardiovascular drug, a metabolic drug, and an antihypertensive drug. In one embodiment, the pharmaceutical drug is selected from the group consisting of ezetimibe, amlodipine besylate, sitagliptin, metformin, atorvastatin, rosuvastatin and simvastatin. In one embodiment, the pharmaceutical composition is formulated as selected from the group consisting of a tablet, a liquid, a gel, a capsule, a sachet, a microparticle, a liposome, a nanoparticle, a salt, a transdermal patch, an ointment, a lotion, a cream, a gel, a drop, a strip, a suppository, a spray and a powder.

In one embodiment, the present invention contemplates a composition comprising a PCSK9 allosteric small molecule ligand. In one embodiment, the composition is a pharmaceutical composition. In one embodiment, the pharmaceutical composition comprises an effective dose of said ligand. In one embodiment, the pharmaceutical composition comprises one or more salts. In one embodiment, the pharmaceutical composition is formulated for oral administration.

In one embodiment, the present invention contemplates a method, comprising: a) administering to a subject a small molecule compound which binds PCSK9 and is an allosteric modulator of the protein, wherein said subject has at least one symptom of a cardiovascular disease; and b) reducing said at least one symptom of cardiovascular disease by said PCSK9 allosteric modulator small molecule compound administration. In one embodiment, said at least one symptom is reduced between 10%-85%. In one embodiment, said at least one symptom is reduced between 20%-65%. In one embodiment, said at least one symptom is reduced between 30%-55%. In one embodiment, the cardiovascular disease comprises a coronary disease. In one embodiment, the cardiovascular disease comprises hypertension. In one embodiment, the cardiovascular disease comprises hypercholesterolemia. In one embodiment, the cardiovascular disease comprises atherosclerosis. In one embodiment, the at least one symptom comprises reduced circulating high density lipoprotein. In one embodiment, the at least one symptom comprises elevated circulating cholesterol. In one embodiment, the at least one symptom comprises elevated circulating low density lipoprotein. In one embodiment, the at least one symptom comprises high blood pressure. In one embodiment, the administering comprises an effective dose of said PCSK9 allosteric modulator small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the allosteric modulator small molecule compound is an organic chemical compound. In one embodiment the allosteric modulator small molecule compound is an organic chemical compound less than 800 Da. In one embodiment the small molecule compound is an organic chemical compound greater than 100 Da and less than 800 Da. In one embodiment the small molecule compound is an organic chemical compound greater than 100 Da and less than 600 Da. In one embodiment the allosteric modulator compound binds PCSK9 with a binding affinity of less than 1 uM. In one embodiment the allosteric modulator compound binds PCSK9 with a binding affinity of less than 500 nM. In one embodiment the allosteric modulator compound binds PCSK9 with a binding affinity of less than 250 nM. In one embodiment the allosteric modulator compound binds PCSK9 with a binding affinity of less than 150 nM. In one embodiment the allosteric modulator compound binds PCSK9 with a binding affinity of less than 100 nM. In one embodiment the allosteric modulator compound binds PCSK9 with a binding affinity of less than 50 nM. In one embodiment the allosteric modulator compound binds PCSK9 with a binding affinity of less than 10 nM. In one embodiment the allosteric modulator compound binds PCSK9 with a binding affinity of less than 1 nM. In one embodiment, the allosteric modulator compound is selected from the group consisting of SRX75, SRX76, SRX200, SRX201, SRX204, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the present invention contemplates a method, comprising: a) administering a PCSK9 allosteric small molecule compound to a subject, wherein said subject has at least one symptom of a liver disease; and b) reducing said at least one symptom of liver disease by said PCSK9 allosteric small molecule compound administration. In one embodiment, the at least one symptom comprises elevated low density lipoprotein receptor density. In one embodiment the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small molecule compound comprises a PCSK9 allosteric inhibitor compound. In one embodiment, the administering comprises an effective dose of said PCSK9 allosteric inhibitor compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises one or more salts. In one embodiment, the pharmaceutical composition is formulated for oral administration. In one embodiment the small molecule compound is an organic chemical compound. In one embodiment the small molecule compound is an organic chemical compound less than 800 Da. In one embodiment the small molecule compound is an organic chemical compound greater than 100 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group including, but not limited to, SRX75, SRX76, SRX200, SRX201, SRX204, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the present invention contemplates a method, comprising: a) administering a PCSK9 allosteric small molecule compound to a subject, wherein said subject has at least one symptom of elevated PCSK9 protein levels in the blood; and b) reducing said at least one symptom of elevated PCSK9 protein levels in the blood by said PCSK9 allosteric small molecule compound administration. In one embodiment, the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small molecule compound comprises a PCSK9 allosteric inhibitor compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small molecule compound is an organic chemical compound. In one embodiment the small molecule compound is an organic chemical compound less than 800 Da. In one embodiment the small molecule compound is an organic chemical compound greater than 100 Da and less than 800 Da. In one embodiment the small molecule compound is an organic chemical compound greater than 100 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group consisting of SRX75, SRX76, SRX204, SRX208, SRX209, SRX210, SRX211, SRX212, SRX 213, SRX214, SRX215, SRX216, SRX217, SRX218, SRX219, SRX220, SRX221, SRX222, SRX223, SRX224, and SRX225.

In one embodiment, the present invention contemplates a method, comprising: a) administering a PCSK9 allosteric small molecule compound to a subject, wherein said subject has at least one symptom of below-average PCSK9 protein levels in the blood; and b) reducing said at least one symptom of depressed PCSK9 by said PCSK9 allosteric small molecule compound administration. In one embodiment, the at least one symptom comprises elevated low density lipoprotein receptor density. In one embodiment, the at least one symptom comprises hypocholesterolemia. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small molecule compound comprises a PCSK9 allosteric activator compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises one or more salts. In one embodiment, the pharmaceutical composition is formulated for oral administration. In one embodiment the small molecule compound is an organic chemical compound. In one embodiment the small molecule compound is an organic chemical compound less than 800 Da. In one embodiment the small molecule compound is an organic chemical compound greater than 100 Da and less than 800 Da. In one embodiment the small molecule compound is an organic chemical compound greater than 200 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group including, but not limited to, SRX200, SRX201, SRX205, SRX206, and SRX207.

In one embodiment, the present invention contemplates a method comprising: a) providing; i) a PCSK9 protein, wherein said protein comprises an allosteric modulation site and an orthosteric low density lipoprotein receptor (LDLR) binding site; and ii) an allosteric small molecule compound capable of binding said allosteric modulation site; and b) binding said allosteric small molecule compound to said allosteric modulation site, wherein said allosteric small molecule compound induces a conformational shift of said orthosteric LDLR binding site. In one embodiment, said binding of said allosteric small molecule compound to said allosteric modulation site, inhibits an induced fit conformational shift of said orthosteric LDLR binding site. In one embodiment, the binding induces a conformational shift of said PCSK9 protein. In one embodiment, the resulting PCSK9 conformational shift reduces the binding affinity of said orthosteric LDLR binding site interaction to a LDLR, wherein low density lipoprotein clearance is increased. In one embodiment, the conformational shift enhances dissociation of said orthosteric low density lipoprotein receptor binding site from a low density lipoprotein receptor. In one embodiment, the conformational shift reduces the orthosteric Cis-His Rich Domain (CHRD) binding site to a binding ligand (e.g., for example, to facilitate vesicle trafficking at low pH; DeVay et al., "Characterization of proprotein convertase subtilisin/kexin type 9 (PCSK9) trafficking reveals a novel lysosomal targeting mechanism via amyloid precursor-like protein 2 (APLP2)" *J Biol Chem.* 288(15):10805-10818 (2013). In one embodiment, the orthosteric low density lipoprotein receptor binding site conformational shift comprises an induced fit inhibition. In one embodiment, the binding of said allosteric small molecule compound reduces the conformational shift required for the induced fit of the orthosteric LDLR binding site of PCSK9, inhibiting the binding affinity of said orthosteric LDLR interaction, wherein low density lipoprotein clearance is increased. In one embodiment, the inducing of said orthosteric low density lipoprotein receptor binding site conformational shift is biomechanical. In one embodiment, the conformational shift results in biomechanical stiffening of the connecting loop between a PCSK9 catalytic domain and a PCSK9 C-terminal domain. In one embodiment, the biomechanical conformational shift comprises a translocational and/or rotational movement of amino acid alanine$^{443}$ side chain and/or backbone. In one embodiment, the biomechanical conformational shift comprises a translocational and/or rotational movement of amino acid valine$^{441}$ side chain and/or backbone. In one embodiment, the biomechanical conformational shift comprises a translocational and/or rotational movement of amino acid aspartic acid$^{422}$ side chain and/or backbone. In one embodiment, the biomechanical conformational shift comprises a translocational and/or rotational movement of amino acid threonine$^{162}$ side chain and/or backbone. In one embodiment, the biomechanical conformational shift comprises a translocational and/or rotational movement of amino acid proline$^{445}$ side chain and/or backbone. In one embodiment, the biomechanical conformational shift comprises a translocational and/or rotational movement of amino acid proline$^{446}$ side chain and/or backbone. In one embodiment, the biomechanical conformational shift comprises a reorientation and translocation of histidine$^{449}$. In one embodiment, the biomechanical mechanism comprises the inhibition of the translocational and/or rotational movement of amino acid alanine$^{443}$ side chain and/or backbone. In one embodiment, the biomechanical mechanism comprises the inhibition of the translocational and/or rotational movement of amino acid valine$^{441}$ side chain and/or backbone. In one embodiment, the biomechanical mechanism comprises the inhibition of the translocational and/or rotational movement of amino acid aspartic acid$^{422}$ side chain and/or backbone. In one embodiment, the biomechanical mechanism comprises the inhibition of the translocational and/or rotational movement of amino acid threonine$^{162}$ side chain and/or backbone. In one embodiment, the biomechanical mechanism comprises the inhibition of the translocational and/or rotational movement of amino acid proline$^{445}$ side chain and/or backbone. In one embodiment, the biomechanical mechanism comprises the inhibition of the translocational and/or rotational movement of amino acid proline$^{446}$ side chain and/or backbone. In one embodiment, the biomechanical shift comprises the inhibition of the translocational and/or rotational movement of histidine$^{449}$ side chain and/or backbone. In one embodiment the small molecule compound is an organic chemical compound. In one embodiment the small molecule compound is an organic chemical compound less than 800 Da. In one embodiment the small molecule compound is an organic chemical compound greater than 100 Da and less than 800 Da. In one embodiment the small molecule compound is an organic chemical compound greater than 100 Da and less than 600 Da. In one embodiment the small molecule compound binds PCSK9 with a binding affinity of less than 1 uM. In one embodiment the small molecule compound binds PCSK9 with a binding affinity of less than 500 nM. In one embodiment the small molecule compound binds PCSK9 with a binding affinity of less than 250 nM. In one embodiment the small molecule compound binds PCSK9 with a binding affinity of less than 150 nM. In one embodiment the small molecule compound binds PCSK9 with a binding affinity of less than 100 nM. In one embodiment the small molecule compound binds PCSK9 with a binding affinity of less than 50 nM. In one embodiment the small molecule compound binds PCSK9 with a binding affinity of less than 10 nM. In one embodiment the small molecule compound binds PCSK9 with a binding affinity of less than 1 nM. In one embodiment, the small molecule compound is selected from the group consisting of SRX75, SRX76, SRX204, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

In one embodiment, the present invention contemplates a compound, SRX204, comprising of the formula:

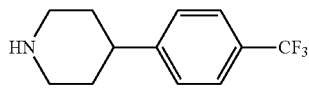 [SMILES: FC(F)(F)c1ccc(C2CCNCC2)cc1]

and preferably the pharmaceutical composition of SRX204.

In one embodiment, the present invention contemplates a pharmaceutical composition comprising a compound of the formula:

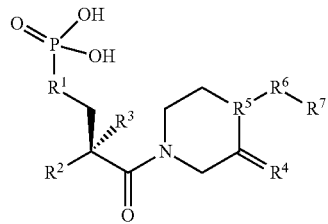

and a carrier, wherein: i) $R^1$ is selected from the group consisting of O, $CH_2$; ii) $R^2$ is selected from the group including an acylated amine (e.g., AcNH—), substituted acyl amine (e.g. AcNHCH($CH_2$OH)CONH—), carbamate (e.g., BnOCONH—), urethane, alkoxyl, branched alkoxy, aryloxyl, substituted aryloxy, 5-membered aromatic heterocycle, substituted 5-membered aromatic heterocycle; iii) $R^3$ is selected from the group consisting of H, OH; iv) $R^4$ is selected from the group consisting of $H_2$, O; v) $R^5$ is selected from the group consisting of C, N; vi) $R^6$ is selected from the group including $CH_2$, O, or nothing; and vii) $R^7$ is selected from the group including aryl, substituted aryl, 5 or 6 membered aromatic heterocycle$_{[O]}$ that is substituted or unsubstituted, cyclic alkyl, 5 or 6 membered non-aromatic heterocycle, branched alkyl, or nothing. In one embodiment the compound is selected from the list consisting of:

SRX75: (S)-2-((S)-2-acetamido-3-hydroxypropanamido)-3-oxo-3-(4-(4-(trifluoromethyl)phenyl)piperidin-1-yl)propyl dihydrogen phosphate;

SRX76: (S)-2-benzamido-3-oxo-3-(4-(4-(trifluoromethyl)phenyl)piperidin-1-yl)propyl dihydrogen phosphate;

(S)-2-isobutyramido-3-oxo-3-(4-(4-(trifluoromethyl)phenyl)piperidin-1-yl)propyl dihydrogen phosphate;

(S)-2-((S)-2-acetamido-3-hydroxypropanamido)-3-oxo-3-(4-(4-(trifluoromethyl)phenyl)piperidin-1-yl)propyl dihydrogen phosphate;

benzyl (S)-(1-oxo-3-(phosphonooxy)-1-(4-(4-(trifluoromethyl)phenyl)piperidin-1-yl)propan-2-yl)carbamate;

(S)-2-(3,3-dim ethylureido)-3-oxo-3-(4-(4-(trifluoromethyl)phenyl)piperidin-1-yl)propyl dihydrogen phosphate;

(S)-2-acetamido-3-oxo-3-(4-(4-(trifluoromethyl)phenyl)piperazin-1-yl)propyl dihydrogen phosphate;

(S)-2-acetamido-3-oxo-3-(4-phenylpiperidin-1-yl)propyl dihydrogen phosphate;

(S)-2-acetamido-3-(4-cyclohexylpiperidin-1-yl)-3-oxopropyl dihydrogen phosphate;

(S)-2-acetamido-3-oxo-3-(4-(pyridin-3-yl)piperidin-1-yl)propyl dihydrogen phosphate;

(S)-2-acetamido-3-(4-(5-methyloxazol-2-yl)piperazin-1-yl)-3-oxopropyl dihydrogen phosphate;

(S)-2-acetamido-3-oxo-3-(4-phenoxypiperidine-1-yl)propyl dihydrogen phosphate;

(S)-2-acetamido-3-(4-(tert-butoxy)piperidin-1-yl)-3-oxopropyl dihydrogen phosphate;

(S)-2-acetamido-3-oxo-3-(4-(4-(trifluoromethyl)phenyl)piperidin-1-yl)propyl hydrogen methylphosphonate (S)-2-(4-ethyl-1H-1,2,3-triazol-1-yl)-3-oxo-3-(4-(4-(trifluoromethyl)phenyl)piperidin-1-yl)propyl dihydrogen phosphate;

(S)-3-oxo-2-phenoxy-3-(4-(4-(trifluoromethyl)phenyl)piperidin-1-yl)propyl dihydrogen phosphate;

(S)-2-isopropoxy-3-oxo-3-(4-(4-(trifluoromethyl)phenyl)piperidin-1-yl)propyl dihydrogen phosphate;

(2S)-2-(5-ethyl-3H-pyrazol-3-yl)-3-oxo-3-(4-(4-(trifluoromethyl)phenyl)piperidin-1-yl)propyl dihydrogen phosphate;

(S)-2-(2-ethyl-2H-tetrazol-5-yl)-3-oxo-3-(4-(4-(trifluoromethyl)phenyl)piperidin-1-yl)propyl dihydrogen phosphate;

(R)-2-(2-ethyl-2H-tetrazol-5-yl)-2-hydroxy-3-oxo-3-(4-(4-(trifluoromethyl)phenyl)piperidin-1-yl)propyl dihydrogen phosphate;

(R)-2-(5-ethyl-1,3,4-oxadiazol-2-yl)-3-oxo-3-(4-(4-(trifluoromethyl)phenyl)piperidin-1-yl)propyl dihydrogen phosphate;

(S)-3-oxo-2-(2H-tetrazol-5-yl)-3-(4-(4-(trifluoromethyl)phenyl)piperidin-1-yl)propyl dihydrogen phosphate;

SRX206: ((S)-3-((S)-2-acetamido-3-hydroxypropanamido)-4-oxo-4-(4-(4-(trifluoromethyl)phenyl)piperidin-1-yl)butyl)phosphonic acid;
(S)-(3-benzamido-4-oxo-4-(4-(4-(trifluoromethyl)phenyl)piperidin-1-yl)butyl)phosphonic acid;
(S)-(3-isobutyramido-4-oxo-4-(4-(4-(trifluoromethyl)phenyl)piperidin-1-yl)butyl)phosphonic acid;
(S)-(3-acetamido-4-oxo-4-(4-(4-(trifluoromethyl)phenyl)piperidin-1-yl)butyl)phosphonic acid;
SRX207: (S)-(3-(((benzyloxy)carbonyl)amino)-4-oxo-4-(4-(4-(trifluoromethyl)phenyl)piperidin-1-yl)butyl)phosphonic acid;
(S)-(3-(3,3-dimethylureido)-4-oxo-4-(4-(4-(trifluoromethyl)phenyl)piperidin-1-yl)butyl)phosphonic acid;
(S)-(3-acetamido-4-oxo-4-(4-(4-(trifluoromethyl)phenyl)piperazin-1-yl)butyl)phosphonic acid;
(S)-(3-acetamido-4-oxo-4-(3-oxo-4-(4-(trifluoromethyl)phenyl)piperazin-1-yl)butyl)phosphonic acid;
(S)-(3-acetamido-4-oxo-4-(4-phenylpiperidin-1-yl)butyl)phosphonic acid;
(S)-(3-acetamido-4-(4-cyclohexylpiperidin-1-yl)-4-oxobutyl)phosphonic acid;
(S)-(3-acetamido-4-oxo-4-(4-(pyridin-3-yl)piperidin-1-yl)butyl)phosphonic acid;
(S)-(3-acetamido-4-(4-(5-methyloxazol-2-yl)piperazin-1-yl)-4-oxobutyl)phosphonic acid;
(S)-(3-acetamido-4-oxo-4-(4-phenoxypiperidin-1-yl)butyl)phosphonic acid;
(S)-(3-acetamido-4-(4-(tert-butoxy)piperidin-1-yl)-4-oxobutyl)phosphonic acid;
(S)-(3-(4-ethyl-1H-1,2,3-triazol-1-yl)-4-oxo-4-(4-(4-(trifluoromethyl)phenyl)piperidin-1-yl)butyl)phosphonic acid;
(S)-(4-oxo-3-phenoxy-4-(4-(4-(trifluoromethyl)phenyl)piperidin-1-yl)butyl)phosphonic acid;
(S)-(3-isopropoxy-4-oxo-4-(4-(4-(trifluoromethyl)phenyl)piperidin-1-yl)butyl)phosphonic acid;
((3R)-3-(5-ethyl-3H-pyrazol-3-yl)-4-oxo-4-(4-(4-(trifluoromethyl)phenyl)piperidin-1-yl)butyl)phosphonic acid;
(R)-(3-(2-ethyl-2H-tetrazol-5-yl)-4-oxo-4-(4-(4-(trifluoromethyl)phenyl)piperidin-1-yl)butyl)phosphonic acid;
(S)-(3-(2-ethyl-2H-tetrazol-5-yl)-3-hydroxy-4-oxo-4-(4-(4-(trifluoromethyl)phenyl)piperidin-1-yl)butyl)phosphonic acid;
(R)-(3-(5-ethyl-1,3,4-oxadiazol-2-yl)-4-oxo-4-(4-(4-(trifluoromethyl)phenyl)piperidin-1-yl)butyl)phosphonic acid;
(R)-2-(2-ethyl-2H-tetrazol-5-yl)-2-hydroxy-3-oxo-3-(4-(4-(trifluoromethyl)phenyl)piperidin-1-yl)propyl dihydrogen phosphate.

In one embodiment, the present invention contemplates a pharmaceutical composition comprising a compound of the formula:

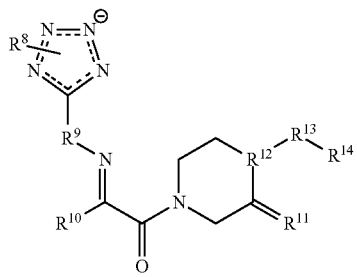

and a carrier, wherein: i) $R^8$ is selected from the group including an alkyl, hydroxyalkyl, substituted alkyl, nothing; ii) $R^9$ is selected from the group consisting of NH and O; iii) $R^{10}$ is selected from the group including an alkyl, branched alkyl, hydroxyalkyl, substituted alkyl, 5 or 6 membered aromatic heterocycle$_{[O]}$ that is substituted or unsubstituted, —CONHR (where R=alkyl, hydroxylalkyl, substituted alkyl, branched alkyl, unsubstituted or unsubstituted aryl or heteroaryl); iv) $R^{11}$ is selected from the group including $H_2$, O; v) $R^{12}$ is selected from the group consisting of C and N; vi) $R^3$ is selected from the group including $CH_2$, O, nothing; and vii) $R^{14}$ is selected from the group including an aryl, substituted aryl, 5 or 6 membered aromatic heterocycle$_{[O]}$ that is substituted or unsubstituted, cyclic alkyl, 5 or 6 membered non-aromatic heterocycle, branched alkyl, nothing. In one embodiment the compound is selected from the list consisting of:

SRX201: (E)-2-(2-(1H-tetrazol-5-yl)hydrazono)-1-(4-(4-(trifluoromethyl)phenyl)piperidin-1-yl)propan-1-one;
SRX200: (E)-2-(2-(1H-tetrazol-5-yl)hydrazono)-1-(4-phenylpiperidin-1-yl)propan-1-one;
(E)-2-(2-(1H-tetrazol-5-yl)hydrazono)-1-(4-(4-(trifluoromethyl)phenyl)piperazin-1-yl)propan-1-one;
(E)-4-(2-(2-(1H-tetrazol-5-yl)hydrazono)propanoyl)-1-(4-(trifluoromethyl)phenyl)piperazin-2-one;
(E)-2-(2-(1H-tetrazol-5-yl)hydrazono)-1-(4-phenylpiperazin-1-yl)propan-1-one;
(E)-2-(2-(1H-tetrazol-5-yl)hydrazono)-1-(4-cyclohexylpiperidin-1-yl)propan-1-one;
(E)-2-(2-(1H-tetrazol-5-yl)hydrazono)-1-(4-phenoxypiperidin-1-yl)propan-1-one;
(E)-2-(2-(1H-tetrazol-5-yl)hydrazono)-1-(4-(pyridin-3-yl)piperidin-1-yl)propan-1-one;
(E)-2-(2-(1H-tetrazol-5-yl)hydrazono)-1-(4-(pyridin-2-yl)piperazin-1-yl)propan-1-one;
(E)-2-(2-(1H-tetrazol-5-yl)hydrazono)-1-(4-(5-methyloxazol-2-yl)piperazin-1-yl)propan-1-one;
(E)-2-(2-(1H-tetrazol-5-yl)hydrazono)-1-(4-(tert-butoxy)piperidin-1-yl)propan-1-one;
(E)-2-(2-(1H-tetrazol-5-yl)hydrazono)-1-(4-phenylpiperidin-1-yl)pentan-1-one;
(E)-2-(2-(1H-tetrazol-5-yl)hydrazono)-3-hydroxy-1-(4-phenylpiperidin-1-yl)propan-1-one;
(Z)-2-(2-(1H-tetrazol-5-yl)hydrazono)-1-(4-phenylpiperidin-1-yl)-2-(thiophen-2-yl)ethan-1-one;
(E)-2-(2-(1H-tetrazol-5-yl)hydrazono)-1-(4-phenylpiperidin-1-yl)-2-(pyridin-2-yl)ethan-1-one;
(E)-2-(2-(1H-tetrazol-5-yl)hydrazono)-N-ethyl-3-oxo-3-(4-phenylpiperidin-1-yl)propanamide;
(E)-2-(2-(2-methyl-2H-tetrazol-5-yl)hydrazono)-1-(4-phenylpiperidin-1-yl)propan-1-one.

In one embodiment, the present invention contemplates a pharmaceutical composition comprising a compound of the formula:

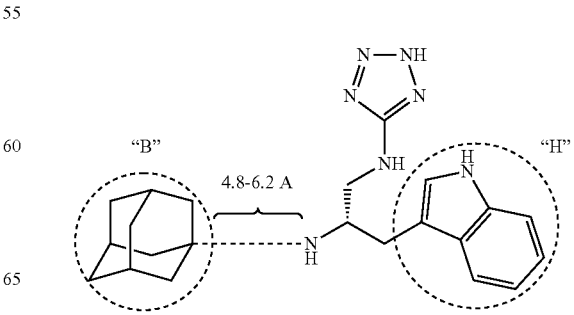

and a carrier, wherein this scaffold consists of a chiral amino tetrazole linked to i) a 5-membered aromatic heterocycle or fused heterocycle "H" and connected through the amino group to ii) a bulky, bridged bicycle "B" 4.8-6.2 Angstroms away. In one embodiment, "B" may be selected from the group including 1-adamantane, 2-adamantane, norbornane, norbornene, N-methyl tropane, other similar bridged carbocycles or heterocycles, or substituted versions thereof. Substitutions may include alcohols, amines, carboxylates, halides, or other common organic moieties. In one embodiment, "H" may be selected from the group including 3-indole, as depicted, or other fused or unfused 5-membered aromatic heterocycles, such as 3-indazole, 3-pyrrole, imidazole, oxazole, oxadiazole, purine. In one embodiment the 4.8-6.2 Angstrom spacer may be peptidic, as described in Scheme 7, or olefin, as described in Scheme 9, or a 5- or 6-membered aromatic, for example of the formula:

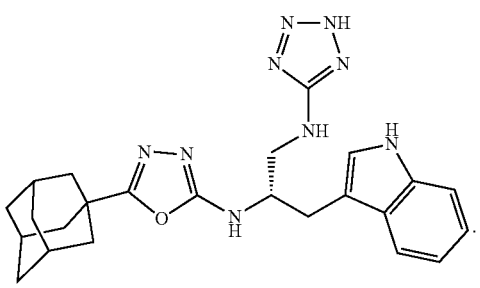 [SMILES: c1ccc2c(C[C@@H](CNc3nn[nH]n3)Nc3nnc(C45CC6CC(CC(C6)C4)C5)o3)c[nH]c2c1]

In one embodiment the compound is selected from the list consisting of:
SRX205: (3S,5S,7S)—N—((S)-1-(((S)-1-((2H-tetrazol-5-yl)amino)-3-(1H-indol-3-yl)propan-2-yl)amino)-3-(4-hydroxyphenyl)-1-oxopropan-2-yl)adamantane-1-carboxamide;
Target 4: (E)-N—((S)-1-((2H-tetrazol-5-yl)amino)-3-(1H-indol-3-yl)propan-2-yl)-3-((1s,3R)-adamantan-1-yl)acrylamide;
(3S,5S,7S)—N—((S)-1-(((S)-1-((2H-tetrazol-5-yl)amino)-3-(1H-1,2,3-triazol-4-yl)propan-2-yl)amino)-3-(4-hydroxyphenyl)-1-oxopropan-2-yl)adamantane-1-carboxamide;
(3S,5S,7S)—N—((S)-1-(((S)-1-((2H-tetrazol-5-yl)amino)-3-(1H-indol-3-yl)propan-2-yl)amino)-1-oxo-3-phenylpropan-2-yl)adamantane-1-carboxamide;
(3S,5S,7)-N—((S)-1-(((S)-1-((2H-tetrazol-5-yl)amino)-3-(1H-indazol-3-yl)propan-2-yl)amino)-3-(4-hydroxyphenyl)-1-oxopropan-2-yl)adamantane-1-carboxamide;
(3S,5S,7S)—N—((S)-1-(((S)-1-((2H-tetrazol-5-yl)amino)-3-(1H-imidazol-4-yl)propan-2-yl)amino)-3-(4-hydroxyphenyl)-1-oxopropan-2-yl) adamantane-1-carboxamide;
(3S,5S,7S)—N((S)-1-(((S)-1-((2H-tetrazol-5-yl)amino)-3-(2-ethyl-1H-imidazol-4-yl)propan-2-yl)amino)-3-(4-hydroxyphenyl)-1-oxopropan-2-yl)adamantane-1-carboxamide;
(1r,5S)—N—((S)-1-(((S)-1-((2H-tetrazol-5-yl)amino)-3-(1H-indol-3-yl)propan-2-yl)amino)-3-(4-hydroxyphenyl)-1-oxopropan-2-yl)bicyclo[3.3.1]nonane-1-carboxamide:
(1R,5S)—N—((S)-1-(((S)-1-((2H-tetrazol-5-yl)amino)-3-(1H-indol-3-yl)propan-2-yl)amino)-3-(4-hydroxyphenyl)-1-oxopropan-2-yl)bicyclo[3.1.1]heptane-3-carboxamide;
(2S)—N2-(3-((1s,3R)-adamantan-1-yl)phenyl)-3-(1H-indol-3-yl)-N1-(2H-tetrazol-5-yl)propane-1,2-diamine;
(2S)—N2-(6-((1s,3R)-adamantan-1-yl)pyridin-2-yl)-3-(1H-indol-3-yl)-N1-(2H-tetrazol-5-yl)propane-1-diamine;
(2S)—N2-(5-((1s,3R)-adamantan-1-yl)-1,3,4-oxadiazol-2-yl)-3-(1H-indol-3-yl)-N1-(2H-tetrazol-5-yl)propane-1,2-diamine;
N—((S)-1-(((S)-1-((2H-tetrazol-5-yl)amino)-3-(1H-indol-3-yl)propan-2-yl)amino)-3-(4-hydroxyphenyl)-1-oxopropan-2-yl)-8-methyl-8-azabicyclo[3.2.1]octane-3-carboxamide;
(1R,2R,4R)—N—((S)-1-(((S)-1-((2H-tetrazol-5-yl)amino)-3-(1H-indol-3-yl)propan-2-yl)amino)-3-(4-hydroxyphenyl)-1-oxopropan-2-yl)bicyclo[2.2.1]hept-5-ene-2-carboxamide;
(1S,2R,4R,5R,6S)—N((S)-1-(((S)-1-((2H-tetrazol-5-yl)amino)-3-(1H-indol-3-yl)propan-2-yl)amino)-3-(4-hydroxyphenyl)-1-oxopropan-2-yl)-5,6-dihydroxybicyclo[2.2.1]heptane-2-carboxamide;
(E)-N—((R)-1-((2H-tetrazol-5-yl)amino)-3-(6-amino-9H-purin-9-yl)propan-2-yl)-3-((1s,3S)-adamantan-1-yl)acrylamide.

In one embodiment the compound is selected from the list consisting of:
SRX204: 4-(4-(trifluoromethyl)phenyl)piperidine;
SRX208: {4-[4-(trifluoromethyl)phenyl]-1-piperazinyl}acetonitrile;
SRX209: 1-[4-(trifluoromethyl)phenyl]piperazine;
SRX210: 4-[3-fluoro-4-(trifluoromethyl)phenyl]piperidine;
SRX211: 4-[3-fluoro-4-(trifluoromethyl)phenyl]piperidine;
SRX212: 4-(4-tert-butylphenyl)piperidine;
SRX213: 4-[4-(trifluoromethyl)phenyl]-4-piperidinol;
SRX214: 4-(4-methylphenyl)piperidine;
SRX215: 2,3,4,4a,9,9a-hexahydro-1H-beta-carboline,
SRX216: 5-chloro-3H-spiro[isobenzofuran-1,4'-piperidine];
SRX217: 6-(tert-butyl)-1,2,3,4-tetrahydroisoquinoline;
SRX218: 3-(p-tolyl)pyrrolidine;
SRX219: 3-(3-(trifluoromethyl)phenyl) pyrrolidine;
SRX220: 4-(piperidin-4-yl)benzoic acid;
SRX221: 4-(4-chlorophenyl)piperazin-2-one;
SRX222: 1-([1,1'-biphenyl]-4-yl)piperazine;
SRX223: 4-phenylcyclohexan-1-amine;
SRX224: 1-(4-chlorophenyl)piperazine;
SRX225: 1-(3-(trifluoromethyl)phenyl)piperazine;
3-(3-tert-butylphenyl)pyrrolidine;
4-(4-piperidinyl)benzamide;
6-(1,1-dimethylethyl)-1,2,3,4-tetrahydroisoquinoline;
1,2,3,4-tetrahydro-6-(2-methylpropyl)-isoquinoline;
1-(4-chlorophenyl)-2,2-dimethylpiperazine;
1-(4-chlorophenyl)-3,3-dimethylpiperazine;
1-(4-chlorophenyl)-2-piperazine;
4-[4-(trifluoromethyl)phenyl]-1-piperazinecarboxylic acid, ethyl ester;
1-[4-(trifluoromethyl)phenyl]-4-piperidinamine;
3-(4-methylphenyl)-pyrrolidine;
4-[4-(trifluoromethyl)phenyl]-cyclohexanamine;
3,5-dimethyl-1-[4-(trifluoromethyl)phenyl]-piperazine;
2-(4-chlorophenyl)-2,5-diazabicyclo[2.2.1]heptane;
4-cyclohexylpiperidine;
4-phenoxypiperidine;
1-(4-(trifluoromethyl)phenyl)piperazine-2,2,6,6-$d_4$.

In one embodiment, the present invention contemplates a pharmaceutical composition comprising a compound of the formula:

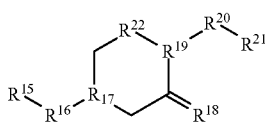

wherein: i) $R^{15}$ is selected from the group consisting of H, alkyl, cyclic alkyl, branched alkyl, and substituted alkyl; ii) $R^{16}$ is selected from the group consisting of nothing and NH; iii) $R^{17}$ is selected from the group consisting of N and CH; iv) $R^{18}$ is selected from the group consisting of $H_2$ and O; v) $R^{19}$ is selected from the group consisting of C and N; vi) $R^{20}$ is selected from the group consisting of nothing, $CH_2$, O, and NH; vii) $R^{21}$ is selected from the group consisting of aryl, substituted aryl, 5 or 6 membered aromatic heterocycle that is substituted or unsubstituted, cyclic alkyl, 5 or 6 membered non-aromatic heterocycle, and branched alkyl; and viii) $R^{22}$ is $CH_2$ or nothing.

In one embodiment, the pharmaceutical composition is further combined with a second pharmaceutical compound. In one embodiment, the second pharmaceutical compound is used as a treatment for hypercholesterolemia. In one embodiment, the second pharmaceutical compound is used as a treatment for a metabolic condition other than hypercholesterolemia. In one embodiment, the pharmaceutical composition is selected from the group including SRX75, SRX76, SRX204, SRX200, SRX201, SRX205, SRX206, SRX207, SRX208, SRX209, SRX210, SRX211, SRX212, SRX213, SRX214, SRX215. SRX216, SRX217, SRX218, SRX219, SRX220, SRX221, SRX222, SRX223, SRX224, and SRX225; and is further combined with a second pharmaceutical compound. In one embodiment, the pharmaceutical composition further comprises a statin. In one embodiment, the statin includes, but is not limited to, atorvastatin, rosuvastatin and/or simvastatin. In one embodiment, the pharmaceutical composition comprises an anti-diabetic drug. In one embodiment, the pharmaceutical composition comprises a cardiovascular drug. In one embodiment, the pharmaceutical composition comprises ezetimibe (Zetia®). In one embodiment, the pharmaceutical composition comprises an anti-hypertensive including, but not limited to, amlodipine besylate (Norvasc®). In one embodiment the anti-diabetic drug includes, but not limited to, sitagliptin (Januvia®) and/or metformin.

In one embodiment, the present invention further contemplates a commercial package comprising (a) a pharmaceutical composition; and (b) instructions for the use thereof for treatment of hypercholesterolemia. In one embodiment, the present invention further contemplates a commercial package comprising (a) a pharmaceutical composition; and (b) instructions for the use thereof for treatment of hypocholesterolemia. In one embodiment, the present invention further contemplates a commercial package comprising (a) a pharmaceutical composition; and (b) instructions for the use thereof for inhibition of PCSK9 protein biological activity. In one embodiment, the present invention further contemplates a commercial package comprising (a) a pharmaceutical composition; and (b) instructions for the use thereof for increasing the biological activity of PCSK9 protein. In one embodiment, the present invention further contemplates a commercial package as a kit.

In one embodiment, the present invention further contemplates a kit comprising (a) a pharmaceutical composition comprising a small molecule compound as contemplated herein; and (b) instructions for the use thereof for treatment of hypercholesterolemia. In one embodiment, the present invention further contemplates a kit comprising (a) a pharmaceutical composition comprising a small molecule compound as contemplated herein; and (b) instructions for the use thereof for treatment of hypocholesterolemia. In one embodiment, the present invention further contemplates a kit comprising (a) a pharmaceutical composition comprising a small molecule compound as contemplated herein; and (b) instructions for the use thereof for inhibition of PCSK9 protein biological activity. In one embodiment, the present invention further contemplates a kit comprising (a) a pharmaceutical composition comprising a small molecule compound as contemplated herein; and (b) instructions for the use thereof for increasing the biological activity of PCSK9 protein. In one embodiment, the present invention further contemplates a kit comprising (a) a pharmaceutical composition selected from the group comprising SRX75, SRX76, SRX204, SRX208, SRX209, SRX210, SRX211, SRX212, SRX 213, SRX214, SRX215, SRX216, SRX217, SRX218, SRX219, SRX220, SRX221, SRX222, SRX223, SRX224, SRX225, and 1-(4-(trifluoromethyl)phenyl)piperazine-2,2,6,6-$d_4$; and (b) instructions for the use thereof for treatment of hypercholesterolemia.

Definitions

The following abbreviations are used throughout the specification:
Bn: benzyl
Bz: benzoyl
Ac: acetyl
Boc: tert-butoxycarbonyl
Fmoc: 9-fluorenylmethoxycarbonyl
Cbz: benzyloxycarbonyl
TFA: trifluoroacetic acid
NMVP: N-methylpyrrolidone
PyBOP: (benzotriazol-1-yloxy)tripyrrolidinophosphoniumhexafluorophosphate
NMM: N-methyl morpholine
HPLC: high pressure liquid chromatography
THF: tetrahydrofuran
DMSO: dimethylsulfoxide
DMF: N,N-dimethylformamide
TMS-Br: trimethylsilyl bromide
Tf: trifluoromethylsulfonyl
HATU: 2-(7-aza-1H-benzotriazole-1-yl)-1,1,3,3-tetramethyluroniumhexafluorophosphate
DIPEA: diisopropylethylamine
DCM: dichloromethane
LAH: lithium aluminum hydride The term "pharmaceutically acceptable salt" as used herein refers to, the free base of the compounds of the present invention can be protonated at any basic nitrogen atoms to form a salt. The term "free base" refers to the amine compounds in non-salt form. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention. The pharmaceutically acceptable salts can be synthesized from the compounds described herein which contain basic moieties by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Thus, pharmaceutically acceptable salts of the instant invention can be prepared from basic compounds described herein by reaction with an inorganic, organic acid or polymeric acid. For example, conventional non-toxic salts include those derived from acids such as hydrochloric acid, acetic acid, toluenesulfonic acid, sulfuric acid, benzenesulfonic acid, fumaric acid or succinic acid. The preparation of the pharmaceutically acceptable salts described above and other typical pharmaceutically acceptable salts is more fully described by Berg et al (1977) J. Pharm. Sci., 'Pharmaceutical Salts', 66:1-19.

The term "hydrate" as used herein, refers to a pharmaceutically acceptable salt form that also contains a stable quantity of water.

The term "solvate" as used herein, refers to a pharmaceutically acceptable salt form that also contains a stable quantity of non-toxic solvent.

The term "small molecule compound" as used herein, refers to an exogenously synthesized organic chemical compound of less than 1,000 Da.

The term "small molecule ligand" as used herein, refers to a small molecule compound that is bound by another naturally occurring biomolecule to form a complex.

The term "conformation" as used herein, refers to a three-dimensional stereochemical configuration of any compound and/or molecule. For example, any specific conformation results from a thermodynamic balance between steric interactions, hydrophobic interactions, hydrogen bonding, electrochemical bonding and/or salt bridge interactions in a protein.

The term "LDL-R" and "LDLR" as used herein, refers to an abbreviation for the low density lipoprotein receptor. The abbreviation may be in reference to the entire LDL-R receptor protein or any portion thereof. LDL-Rs reside on a cell surface and can bind to low density lipoproteins such that the LDL-R/LDL complex become internalized within a cell (i.e., for example, a hepatocyte), wherein the LDL is released and the LDL-R is recycled back to the cell surface.

The term, "binding interface" as used herein, refers to any collection of attractive interactions (i.e., for example, hydrogen bonding, electrostatic interactions, hydrophobic interactions, etc) between the functional groups (i.e., for example, hydroxyl, amide, amine, carboxyl, amidine, guanidine, hydrocarbon, sulfonyl etc.) of at least two different molecules. The collection of attractive forces forms a stable molecular plane thereby forming a 'binding interface' between the at least two molecules.

The term "induced fit" as used herein, refers to any acceptance of a small molecule compound requiring a change in the receiving molecule's conformation. Such a conformation may be facilitated by a translational/rotational movement of amino acid side chains and flexible loops, thereby rearranging the electrostatic and/or hydrophobic fields.

The term "complex" or "composition" as used herein, refers to any chemical association of two or more ions or molecules joined usually by weak electrostatic bonds rather than by covalent bonds. For example, a complex or composition may be formed between a small molecule compound as described herein and a PCSK9 amino acid sequence, thereby creating a small molecule compound: PCSK9 amino acid sequence complex or composition. Optionally, such complexes or compositions may also include, but are not limited to, an LDLR amino acid sequence or any portion thereof, including but not limited to the EGFA region.

The term "hydrogen bond" as used herein, an electrostatic attraction between a hydrogen atom in one polar molecule (as of water) and a small electronegative atom (as of oxygen, nitrogen, or fluorine) in usually another molecule of the same or a different polar substance.

The term "salt bridge" as used herein, refers to any interaction or a combinations of interactions, such as hydrogen bonding and/or electrostatic interactions, which align cationic and anionic chemical structures in such a way that the charged moieties overlap.

The term "interaction" as used herein, refers to any effect that one molecule and/or functional group may have on another molecule and/or functional group. Such effects may include, but are not limited to, steric (i.e., for example, physical), electrostatic (i.e., for example, electrical attraction or repulsion), electromagnetic, hydrophilic, or hydrophobic effects.

The term "overlap" as used herein, refers to any positioning of molecules in such a way that the electronic structure of one molecule is on top of, and extending past the border of another molecule, or be positioned in this way.

The term "hypercholesterolemia" as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 70 mg/dl. Alternatively, if cholesterol is measured using free plasma cholesterol, hypercholesterolemia may exist if the measured free cholesterol levels are above, for example, approximately 200-220 mg/dl.

The term "hypocholesterolemia" as used herein, refers to any medical condition wherein blood cholesterol levels are below clinically recommended levels. For example, if total cholesterol or LDL-C levels are measured as below the $5^{th}$ percentile of the general population after adjustment for gender, race, and age.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" and/or "disorder", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The term "affinity" as used herein, refers to the measure of the thermodynamic tendency of two or more molecules to assemble to form a multi-part complex and to remain assembled in said complex. For example, a small molecule ligand has a high affinity for PCSK9 and is thermodynamically favored to form a complex. It is understood that a change in conditions (e.g., pH during the receptor internalization process) may reduce the affinity of the molecules such that they dissociate, or separate, from one another. For example, pH changes can result in a decrease in the LDL affinity for LDLR and subsequent dissociation of that complex.

The term "derived from" as used herein, refers to the source of a compound. In one respect, a compound may be derived from an organism or particular species. In another respect, a compound may be derived from a larger complex. In another respect, a compound may be derived by chemical modification of part or all of a larger complex.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur, and forming a contiguous protein backbone. In general, a protein comprises amino acids having an order of magnitude within the hundreds.

The term "peptide" as used herein, refers to any of various amides that are derived from three or more amino acids by combination of the amino group of one acid with the carboxyl group of another and are usually obtained by partial hydrolysis of proteins. In general, a peptide comprises amino acids having an order of magnitude within the tens or smaller.

The term, "purified" or "isolated", as used herein, may refer to a composition that has been subjected to treatment (i.e., for example, fractionation) to remove various other components, and which composition substantially retains its expressed biological activity.

Where the term "substantially purified" is used, this designation will refer to a composition in which a small molecule compound forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single small molecule compound species (i.e., for example, based upon SDS-PAGE or HPLC analysis). A purified composition is not intended to mean that all trace impurities have been removed.

As used herein, the term "substantially purified" refers to molecules, such as small molecule compound, that are removed from their natural environment, isolated or separated, and are at least 60% free, preferably 75% free, and more preferably 90% free from other components with which they are naturally associated.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The terms "amino acid sequence" and "polypeptide sequence" as used herein, are interchangeable and to refer to a contiguous sequence of multiple amino acids.

The term "derivative" as used herein, refers to any chemical modification of a small molecule compound. Examples of such modifications would include, but are not limited to, replacement of a hydrogen by an alkyl, aryl, hydroxyl, sulfhydryl, sulfoxyl, sulfonyl, acyl, phosphoryl, alkoxyl, amino or amino heterocyclic group. Other possible chemical modification might include, but are not limited to, C-terminal amides, and acyl or sulfonyl N-terminal modifications.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte/target being measuring/affected. The "binding" interaction may be brief as in the situation where binding causes a chemical reaction to occur. That is typical when the binding component is an enzyme and the analyte/target is a substrate for the enzyme. Reactions resulting from contact between the binding agent and the analyte/target are also within the definition of binding for the purposes of the present invention.

Chemical Terminology

Alkyl: a chain consisting of only carbon and hydrogen atoms such that each carbon atom directly connects to exactly 4 different atoms, using only single bonds.
Lower alkyl: an alkyl chain containing 1-6 carbon atoms.
Branched alkyl: an alkyl chain containing one or more carbon atoms which are directly connected to more than 2 other carbon atoms without creating a ring of carbon atoms.
Hydroxyalkyl: an alkyl chain where at least one carbon atom is bonded to a hydroxyl, that is, —OH.
Cycloalkyl: an alkyl chain forming a ring. Examples would include —CH2-cyclopropyl or -cyclohexyl.
Heterocycle: a chain of atoms forming a ring and containing one or more "heteroatoms"; that is, atoms other than C or H able to form stable covalent bonds, such as N, O, or S. In this context, "heterocyle" will imply a non-aromatic ring. Examples include a tetrahydrofuran ring, with 4 carbon atoms and one oxygen, or a morpholine, with 4 carbon atoms and one nitrogen and one oxygen arranged such that the N and O are 1,4 to one another.
Aromatic ring: a ring of atoms containing alternating single and double "pi" bonds such that the number pi electrons (typically 2 per double bonds for stable compounds) is an even number but not a multiple of four.
Heteroaryl: an aromatic ring at least one heteroatom. In this context, the heteroaryl will imply a 3-6 membered ring.
Acyl: a carbonyl containing radical: —CO—R. In this document, R=affords a typical peptide modifying group, such as: —CH3 (acetyl), —CH(CH2)2 (isobutyryl).
Benzoyl: a carbonyl containing radical: —CO-Ph, where Ph=phenyl.
Sulfonyl: a sulfonyl containing radical: —SO2-R.
Carbamoyl: a radical: —CONR1R2
Alkoxy: an alkyl chain containing one or more ether (—O—) linkages, such as: —CH2CH2OCH3.
Aryl: phenyl or substituted phenyl
Heteroaryl: a 5 or 6 membered aromatic heterocycle
Fused heterocycle: a ring system, such as indole, containing two or more fused rings, of which at least one is a heterocycle. The rings need not be aromatic: indoline has an aromatic ring fused to a non-aromatic ring.

Negatively charged polar group: A polar group carrying a negative charge at physiologic pH.

DETAILED DESCRIPTION OF THE INVENTION

Figure 1:
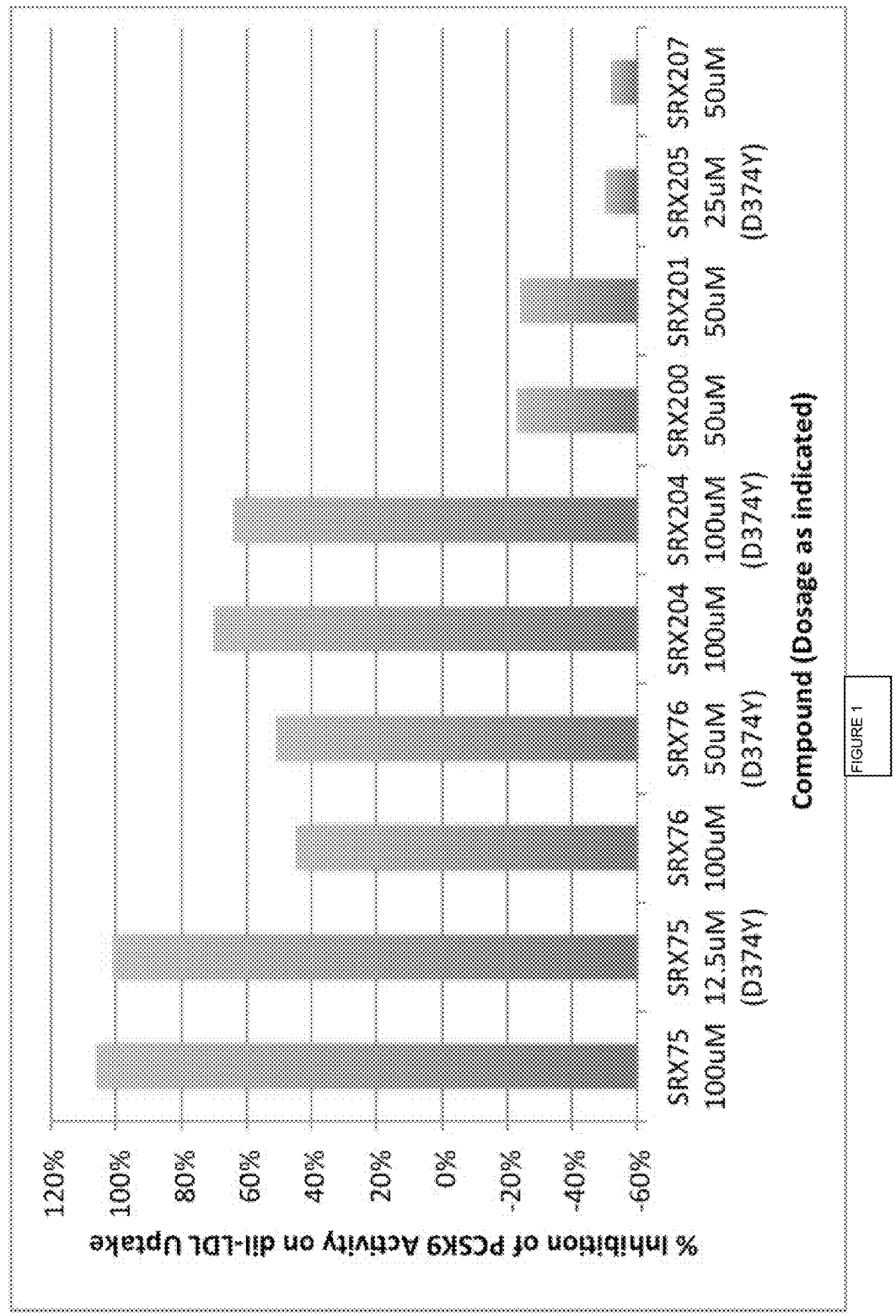
FIG. 1 shows exemplary data of % PCSK9 modulation in HepG2 cells. The cells were incubated in a 96-well plate for a total of 20 h in the absence or presence PCSK9 protein alone (mutant D374Y: 2 nM; WT: 10 nM) or protein, pre-mixed and pre-incubated for 4 hours, with indicated uM concentration of SRX compounds. After 16 h, DiI-LDL (5 ug/ml) was added to the incubation mixtures. After 4 h, fluorescence was measured (Ex: 520 nm/Em: 575 nm; cutoff: 550 nm). The % inhibition (>0%) or activation (<0%) of the PCSK9 activity on DiI-LDL uptake was calculated from relative fluorescence.
Figure 2:
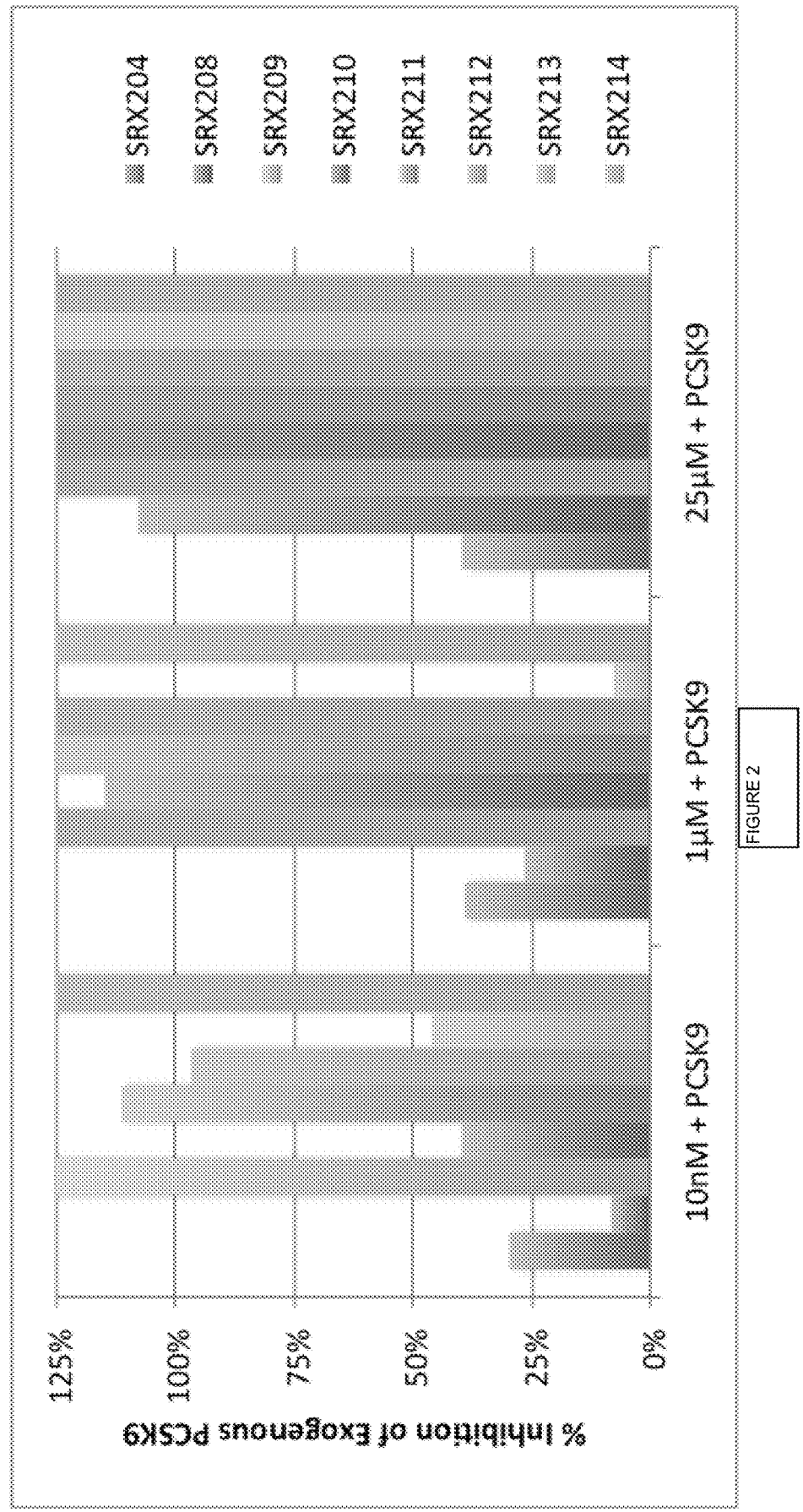
FIG. 2 shows exemplary data of % PCSK9 inhibition in HuH7 cells. The cells were incubated in 12-well plates for a total of 6 h in the absence or presence of PCSK9 protein (10 nM), or in the presence of PCSK9 protein mixed with indicated concentration of SRX compound. After 6 hours, the cells were released from the plate, treated with anti-LDLR antibody for 1 hour, then rinsed, counterstained with 7AAD, and then measured by fluorescence activated cell sorting (FACS). Inhibition was calculated as ['Specimen LDLR Fluorescence'–'10 nM PCSK9 Fluorescence']/['No PCSK9 Basal Fluorescence'–'10 nM PCSK9 Fluorescence']×100%.
Figure 3:
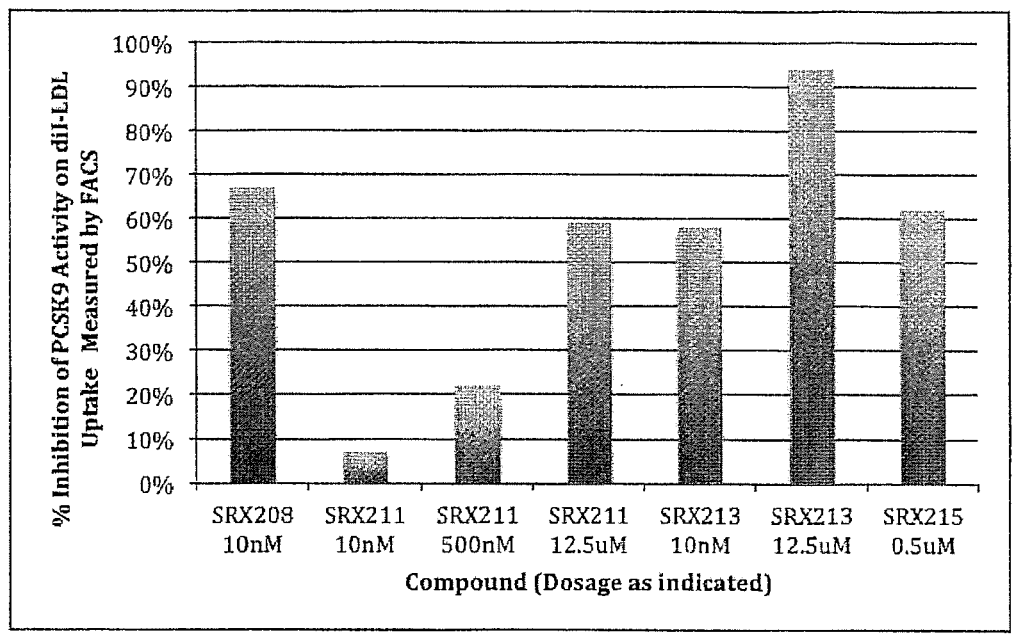
FIG. 3 shows exemplary data of % PCSK9 inhibition in HuH7 cells. The cells were incubated in a 12-well plate for a total of 6 h in Lipoprotein Deficient Serum with DiI-LDL at a final concentration of 5 ug/ml in the absence or presence PCSK9 protein alone (10 nM) or the presence of protein with indicated concentration of SRX compounds. After 6 h, cells were released from the plate, counterstained with 7AAD, and then measured by fluorescence activated cell sorting (FACS). The % inhibition of the PCSK9 activity on DiI-LDL uptake was calculated from relative fluorescence recovery in the presence of compound versus fluorescence decreased due to PCSK9 alone, described in equation form as ['Tested Compound Fluorescence'–'10 nM PCSK9 Fluorescence']/['No PCSK9 Basal Fluorescence'–'10 nM PCSK9 Fluorescence']×100%.
Figure 4:
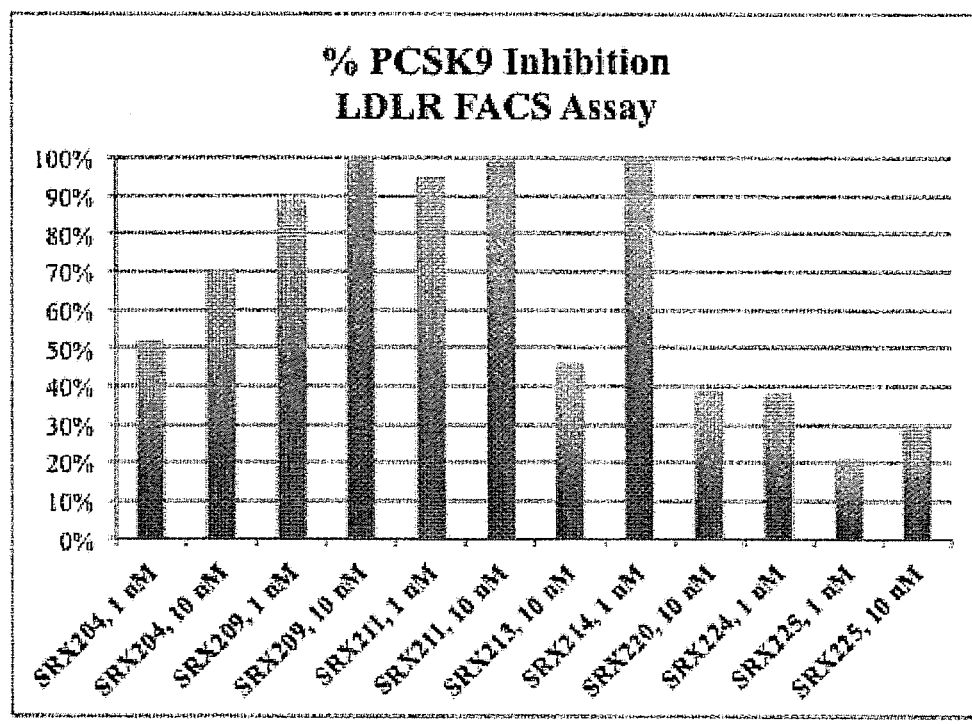
FIG. 4 shows exemplary data of % PCSK9 inhibition in HuH7 cells, as measured by cell surface LDLR expression by FACS. Cells were cultured in 12-well plates for approximately 24 hours, followed by treatment with 10 nM of recombinant PCSK9 plus dosage with the indicated concentration of SRX compound. After a 6-hour incubation period, cells were rinsed, collected, stained with an anti-LDLR antibody and a cell viability stain, and then measured by flow cytometry (aka fluorescence activated cell sorting—FACS). PCSK9% inhibition was calculated as the % amount LDLR recovery with normalized by the LDLR drop caused by 10 nM of recombinant PCSK9.

This invention is related to the field of PCSK9 biology and use of compounds for treatment including conditions of hypercholesterolemia and hypocholesterolemia. In particular, the invention provides compositions of ligands that bind and alter PCSK9 biological conformation and activity. These ligands are small molecule chemical compounds, and more preferably small molecule compounds less than 800 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

I. Physiological Role of Native PCSK9

Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation" *Proc. Natl. Acad. Sci. U.S.A.* 100 (3): 928-933 (2003). Similar genes (orthologs) are found across many species. Many enzymes, including PSCK9, are inactive when they are first synthesized, because they have a section of peptide chains that blocks their activity; proprotein convertases remove that section to activate the enzyme.

The PSCK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence (SEQ ID NO: 1) is:

```
001  mgtvssrrsw  wplplllll  lllgpagara  qededgdyee lvlalrsced  glaeapehgt 061  tatfhrcakd  pwrlpgtyvv  vlkeethtsq  sertarrlqa qaarrgyltk  ilhvfhgllp 121  gflvkmsgdl  lelalklphv  dyieedssvf  aqsipwnler itppryrade  yqppdggslv 181  evylldtsiq  sdhreiegrv  mvtdfenvpe  edgtrfhrqa skcdshgthl  agvvsgrdag 241  vakgasmrsl  rvlncqgkgt  vsgtliglef  irksqlvqpv gplvvllpla  ggysrvlnaa 301  cqrlaragvv  lvtaagnfrd  daclyspasa  pevitvgatn aqdqpvtlgt  lgtnfgrcvd 361  lfapgediig  assdcstcfv  sqsgtsqaaa  hvagiaamml saepeltlae  lrqrlihfsa 421  kdvineawfp  edqrvltpnl  vaalppsthg  agwqlfcrtv wsahsgptrm  atavarcapd 481  eellscssfs  rsgkrrgerm  eaqggklvcr  ahnafggegv yaiarccllp  qancsvhtap 541  paeasmgtrv  hchqqghvlt  gcsshweved  lgthkppvlr prgqpnqcvg  hreasihasc 601  chapgleckv  kehgipapqe  qvtvaceegw  tltgcsalpg tshvlgayav  dntcvvrsrd 661  vsttgstseq  avtavaiccr  srhlaqasqe  lq (Accession No. NP_777596).
```

PSCK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

As it is estimated that approximately 9 million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (i.e., for example, by increasing the availability of LDL-Rs and, consequently, LDL-C clearance). Such drugs are beginning Phase III clinical trials to assess their safety and efficacy in humans, and to determine if they can improve outcomes in heart disease.

Drugs that inhibit LDL-R/PCSK9 complex formation have been suggested to lower cholesterol much more than conventionally available cholesterol-lowering drugs (i.e., for example, statins). It is biologically plausible that this would also lower heart attacks and other diseases caused by raised cholesterol. Studies with humans, including phase III clinical trials now underway, are focused as to whether PCSK9 inhibition actually does lower cardiovascular disease, with acceptable side effects. Lopez D., "Inhibition of PCSK9 as a novel strategy for the treatment of hypercholesterolemia" *Drug News Perspect.* 21(6): 323-e30 (2008); Steinberg et al., "Inhibition of PCSK9: a powerful weapon for achieving ideal LDL cholesterol levels" *Proc. Natl. Acad. Sci. U.S.A.* 106(24): 9546-9547 (2009); Mayer, "Annexin A2 is a C-terminal PCSK9-binding protein that regulates endogenous low density lipoprotein receptor levels" *J. Biol. Chem.* 283(46): 31791-31801 ((2008); and Anonomyous, "Bristol-Myers Squibb selects Isis drug targeting PCSK9 as development candidate for prevention and treatment of cardiovascular disease" *Press Release. FierceBiotech.* 2008 Apr. 8.

Currently, it has been reported that PCSK9 antibody drugs are in clinical trials (e.g., for example, Sanofi/Regeneron, Amgen, Pfizer, Novartis, Roche). However, one disadvantage of antibody therapy is that the administration is performed by subcutaneous or intravenous injection. A number of monoclonal antibodies that bind to PCSK9 near the catalytic domain that interact with the LDL-R and hence inhibit LDL-RPCSK9 complex formation are currently in clinical trials. These antibodies include AMGI45 (Amgen), 1D05-IgG2 (Merck & Co.), and SAR236553/REGN727 (Aventis/Regeneron). Lambert et al., "The PCSK9 decade" *J. Lipid Res.* 53(12): 2515-2524 (2012).

Peptides that mimic the EGF-A domain of the LDL-R have been developed to inhibit LDL-RPCSK9 complex formation. Shan et al., "PCSK9 binds to multiple receptors and can be functionally inhibited by an EGF-A peptide". *Biochem. Biophys. Res. Commun.* 375(1): 69-73 (2008). Peptidic PCSK9 inhibitors of the EGF-A binding site were identified by screening both linear and disulfide-constrained phage-displayed peptide libraries. This approach identified a 13-amino acid peptide (Pep2-8) that includes structural mimicry of the natural binding domain of LDL receptor. The peptide inhibitor binding site was determined to largely overlap with that of the EGF(A) domain; therefore, Pep2-8 acts a competitive inhibitor of LDL receptor binding. This is akin to the inhibition mechanism of anti-PCSK9 monoclonal antibodies, which also disrupt the interaction of the LDL receptor-EGF(A) domain with PCSK9. Zhang et al., "Identification of a Small Peptide That Inhibits PCSK9 Protein Binding to the Low Density Lipoprotein Receptor" *J Biol Chem* 289:942-955 (2014).

PCSK9 antisense oligonucleotides (Isis Pharmaceuticals) have been shown to increase expression of the LDL-R and decrease circulating total cholesterol levels in mice. Graham et al., "Antisense inhibition of proprotein convertase subtilisin/kexin type 9 reduces serum LDL in hyperlipidemic mice" *J. Lipid Res.* 48(4): 763-767 (2007). It has also been reported that a locked nucleic acid (Santaris Pharma) reduced PCSK9 mRNA levels in mice. Gupta et al., "A locked nucleic acid antisense oligonucleotide (LNA) silences PCSK9 and enhances LDLR expression in vitro and in vivo" *PLoS ONE* 5(5): e10682 (2010); and Lindholm et al., "PCSK9 LNA antisense oligonucleotides induce sustained reduction of LDL cholesterol in nonhuman primates". *Mol. Ther* 20(2):376-381 (2012). Initial clinical trials of an RNAi (ALN-PCS, Alnylam Pharmaceuticals) has shown positive results as an effective means of inhibiting LDL-R/PCSK9 complex formation. Frank-Kamenetsky et al., "Therapeutic RNAi targeting PCSK9 acutely lowers plasma cholesterol in rodents and LDL cholesterol in nonhuman primates" *Proc. Natl. Acad. Sci. U.S.A.* 105(33): 11915-11920 (2008).

II. PCSK9 Allosteric Site Modulation Small Molecule Compounds

Variants of PCSK9 can reduce or increase circulating cholesterol. Abifadel et al., "Mutations in PCSK9 cause autosomal dominant hypercholesterolemia" *Nat. Genet.* 34 (2): 154-156 (2003). LDL-C is normally removed from the blood when it binds to an LDL-R on the surface of liver cells, and is internalized within the hepatocyte as a receptor-ligand complex. However, when PCSK9 binds to an LDL-R, the LDL-R is concomitantly degraded along with the complexed LDL particle. However, if a PCSK9 is not bound to an LDL-R, the LDL-R is recycled after internalization thereby returning to the surface of the cell for removal of more cholesterol.

In some embodiments, the invention relates to small molecule compounds having a modulation effect on PCSK9's ability to form an LDL-R/PCSK9 complex. In some embodiments, the present invention contemplates the use of small molecule compounds that bind to a PCSK9 protein and modulate the protein's biological activity. In some embodiments, the small molecules decrease LDL-R/PCSK9 complex formation and are thereby useful to treat various diseases comprising lipid dysregulation. In some embodiments, the small molecules increase LDL-R/PCSK9 complex formation and are thereby useful in research and development of therapies relevant to LDL dysregulation.

Although it is not necessary to understand the mechanism of an invention, it is believed that "gain-of-function" (GOF) PCSK9 mutants may result in conditions including, but not limited to, hypercholesterolemia. For example, compounds that bind to a PCSK9 and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Although it is not necessary to understand the mechanism of an invention, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, small molecule compounds that bind to a PCSK9 that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The presently disclosed embodiments of PCSK9 binding small molecule compounds have several advantages over current peptides and ligands described in the art. For example, small molecule PCSK9 binding compounds, as contemplated herein, have the advantage that these compounds are smaller than many previously described peptides. It is envisioned that these small molecule compounds can be administered orally without immunological reactions seen with antibody administration, or systemic degradation problems as seen with nucleic acid administration (i.e., antisense or locked nucleic acids). Nonetheless, as these small compounds have long half-lives, encapsulation drug delivery systems, such as liposomes or other biodegradable protective compositions, will lengthen these half-lives to a greater extent than either antibodies or nucleic acids. These small molecule compounds described in this application are designed de novo to have desirable characteristics, such as for drug-like properties.

III. Clinical Therapeutics

In some embodiments, the present invention contemplates the administration of a small molecule PCSK9 allosteric inhibitor compound to a subject having a symptom of a cardiovascular disease. In one embodiment, the cardiovascular disease comprises hypercholesterolemia. In one embodiment, the cardiovascular disease comprises hypertension. In one embodiment, the hypercholesterolemia comprises elevated low density lipoprotein levels.

In some embodiments, the present invention contemplates the administration of a small molecule PCSK9 allosteric inhibitor compound to a subject having a symptom of a metabolic disease. In one embodiment, the metabolic disease comprises diabetes.

Although it is not necessary to understand the mechanism of an invention, it is believed that the administration of a PCSK9 allosteric inhibitor small molecule compound (i.e., such as those described herein) induces a conformational shift of the PCSK9 protein such that the affinity of the low density lipoprotein binding site for a low density lipoprotein receptor is decreased, wherein PCSK9/LDL-R complex formation is decreased. The decrease in PCSK9/LDL-R complex formation results in an increase in the bioavailability of LDL-R receptors for binding to circulating LDL, thereby increasing the internalization and clearance of LDL by LDL-R. It is further believed that a small molecule PCSK9 allosteric inhibitor compound may result in increased bioavailability of hepatocyte cell LDL-Rs.

Further, although it is not necessary to understand the mechanism of an invention, it is believed that the administration of a PCSK9 allosteric activator small molecule compound (i.e., such as those described herein) induces a conformational shift of the PCSK9 protein such that the affinity of the low density lipoprotein binding site for a low density lipoprotein receptor is increased, wherein PCSK9/LDL-R complex formation is increased or stabilized. The increase or stabilization in PCSK9/LDL-R complex formation results in a decrease in the bioavailability of LDL-R receptors for binding to circulating LDL, thereby decreasing the internalization and clearance of LDL by LDL-R. It is further believed that a PCSK9 allosteric activator compound may result in decreased bioavailability of hepatocyte cell LDL-Rs.

A. Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" *The Lancet* 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" *BMJ* 337: a993. Genetic abnormalities are in some cases completely responsible for hypercholesterolemia, such as in familial hypercholesterolemia where there is one or more genetic mutations in the autosomal dominant APOB gene, the autosomal recessive LDLRAP1 gene, autosomal dominant familial hypercholesterolemia (HCHOLA3) variant of the PCSK9 gene, or the LDL receptor gene. "Hypercholesterolemia" *Genetics Home Reference* U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia". *eMedicine Medscape*, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" *Adv Physiol Educ* 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" *Circulation* 109(23 Suppl 1): III 2-7. In contrast, higher levels of HDL cholesterol are protective. Kontush et al., (2006) "Antiatherogenic small, dense HDL—guardian angel of the arterial wall?" *Nat Clin Pract Cardiovasc Med* 3(3):144-153. Elevated levels of non-IDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood: These fats are called lipids. There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" *BMJ* 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn A V, Nakano M, Narula J, Kolodgie F D, Virmani R (July 2010). "Concept of vulnerable/unstable plaque" *Arterioscler. Thromb. Vasc. Biol.* 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" *Circulation* 97(18):1876-1887.

B. Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" *Circulation* 86 (3): 1046-1060; and Suarez E. C., (1999) "Relations of trait depression and anxiety to low lipid and lipoprotein concentrations in healthy young adult women". *Psychosom Med* 61(3): 273-279. It is also possible that whatever causes the low cholesterol level also causes mortality, and that the low cholesterol is simply a marker of poor health.

C. Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy.

Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

IV. Pharmaceutical Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, (e.g., intrathecal or intraventricular), administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral, sublingual or buccal administration include powders or granules, suspensions or solutions in water or non-aqueous media, capsules, gels, drops, strips, gums, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

In some embodiment, the pharmaceutical compositions may further comprise other drugs and/or hormones. For example, the pharmaceutical composition may further comprise a statin drug. Statins (or HMG-CoA reductase inhibitors) are a class of drugs used to lower cholesterol levels by inhibiting the enzyme HMG-CoA reductase, which plays a role in the production of cholesterol in the liver. Increased cholesterol levels have been associated with cardiovascular diseases, and statins are therefore used in the prevention of these diseases. Lewington et al., "Blood cholesterol and vascular mortality by age, sex, and blood pressure: a meta-analysis of individual data from 61 prospective studies with 55,000 vascular deaths" Lancet 370(9602): 1829-1839 (2007). Research has found that statins are most effective for treating cardiovascular disease (CVD) as a secondary prevention strategy, with questionable benefit in those with elevated cholesterol levels but without previous CVD. Taylor et al. "Statins for the primary prevention of cardiovascular disease". In: Taylor, Fiona. Cochrane Database Syst Rev (1) (2011). Statins have rare but severe adverse effects, particularly muscle damage.

Specific examples of statins include, but are not limited to, atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). Several combination preparations of a statin and another agent, such as ezetimibe/simvastatin, are also available.

Specific examples of cardiovascular drugs include, but are not limited to, propranolol, digitalis, amlodipine besylate, and nifedipine.

Specific examples of other pharmaceutical compositions may further include, but are not limited to, exetimibe (Zetia®), amlodipine besylate (Norvasc®), niacin, sitagliptin (Januvia®), metformin or orlistat (Alli®/Xenical®).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical ingredient(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the small molecule compounds described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the small molecule compound is administered in maintenance doses, ranging from 0.01 μg to 100 g per kg of body weight, once or more daily, to once every 20 years.

In one embodiment, the present invention further contemplates a commercial package comprising (a) a pharmaceutical composition; and (b) instructions for the use thereof for treatment of hypercholesterolemia. In one embodiment, the present invention further contemplates a commercial package comprising (a) a pharmaceutical composition; and (b) instructions for the use thereof for treatment of hypocholesterolemia. In one embodiment, the present invention further contemplates a commercial package comprising (a) a pharmaceutical composition; and (b) instructions for the use thereof for inhibition of PCSK9 protein biological activity. In one embodiment, the present invention further contemplates a commercial package comprising (a) a pharmaceutical composition; and (b) instructions for the use thereof for increasing the biological activity of PCSK9 protein.

V. Description of Chemistry

Schemes 1-4 referred to as Generic Structure 1, comprises an amide scaffold as shown below:

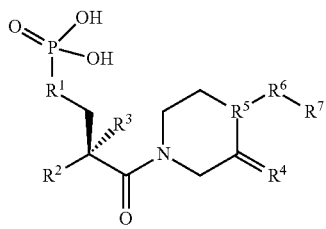

SRX75 (Example V) was synthesized using solid phase resin techniques described in the example section.

(9H-fluoren-9-yl)methyl ((2S)-1-hydroxy-3-(((benzyloxy)(hydroxy)phosphoryl)oxy)-1-oxopropan-2-yl)carbamate was attached to a solid phase resin. The Fmoc protecting group was removed and the N-terminus was reacted with (S)-2-acetamido-3-(tert-butoxy)propanoic acid using coupling reagents. The resulting intermediate was removed from the resin and coupled at the C-terminus with 4-(4-(trifluoromethyl)phenyl)piperidine). The protecting groups were removed. A variety of resins, protecting groups, coupling reagents could be used to achieve the desired transformations.

SRX206 (Example VI) was prepared from a known Cbz-protected phosphonate scaffold (Caroff, et al, U.S. Pat. No. 8,518,912, 2013), outlined in Scheme 1. The Cbz-protected phosphonate acid scaffold was coupled to 4-(4-(trifluoromethyl)phenyl)piperidine using coupling reagents. The Cbz group was removed by hydrogenation and acylation was achieved using routine chemistry. The desired phosphonic acid was liberated using TMS-Br to remove the ethyl moieties.

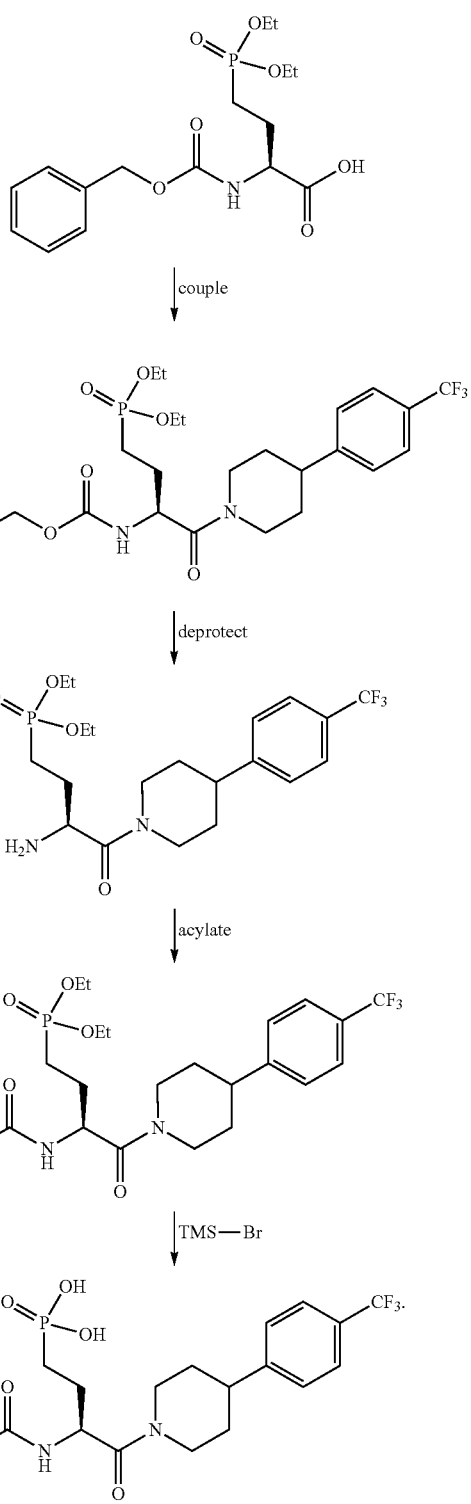

Alternatively, the amine moiety ($R^2$) could be replaced with a variety of aromatic and non-aromatic substituents. Scheme 2 shows a method for using cycloaddition of an azide created from the N-terminus amine using known chemistry to create a triazole in the $R^2$ position (see Burgess, US 2009/0264315 A1, 2009).

Scheme 2:

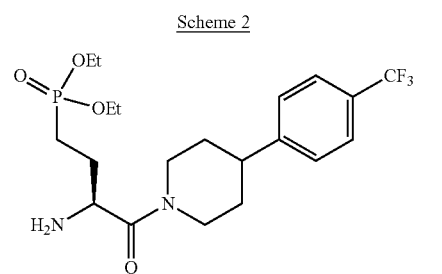

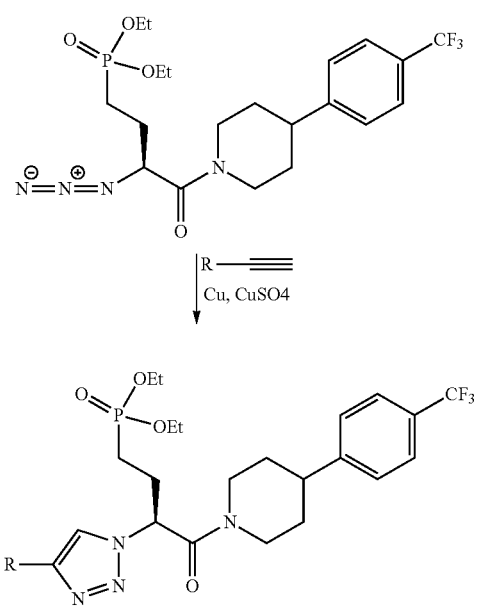

Scheme 3 demonstrates how an alpha carboxylate could be used to create other simple heterocycles in the $R^2$ position; in this figure, an oxadiazole. The alpha carboxy group could be introduced by deprotonating the methylene next to the amide and quenching with $CO_2$.

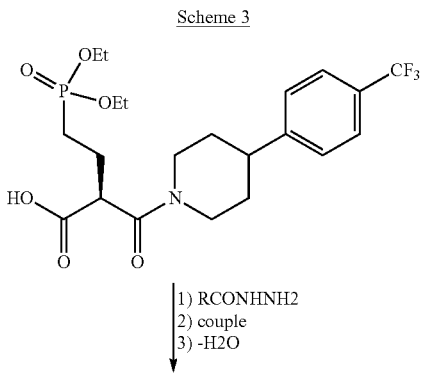

-continued

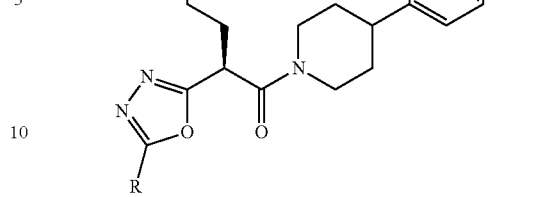

Finally, Scheme 4 illustrates how an alpha leaving group could be displaced by a nucleophile, such as aryloxy-. The alpha bromo could be obtained by a variety of methods. For example, the methylene next to the amide could be deprotonated and quenched with $Br_2$.

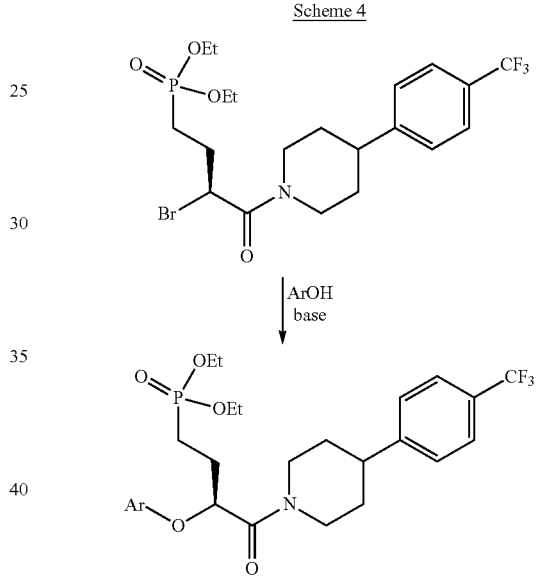

Schemes 5-6 refer to Generic Structure 2, shown below, a scaffold consisting of a 5-aminotetrazole hydrazone alpha to a carboxamide.

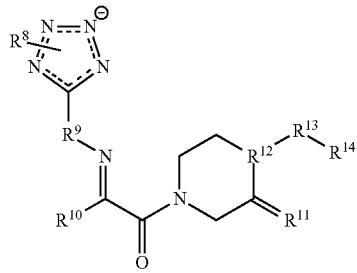

SRX201 (Example VII), a tetrazole-substituted hydrazone, was synthesized as shown in scheme 5. Reaction of the tetrazole hydrazine with pyruvic acid affords the hydrazone, which is reacted using amide coupling reagents to give the desired amide.

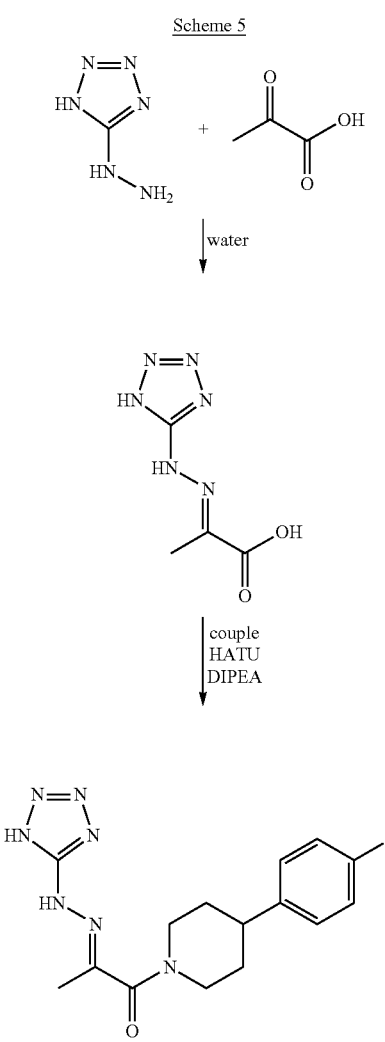

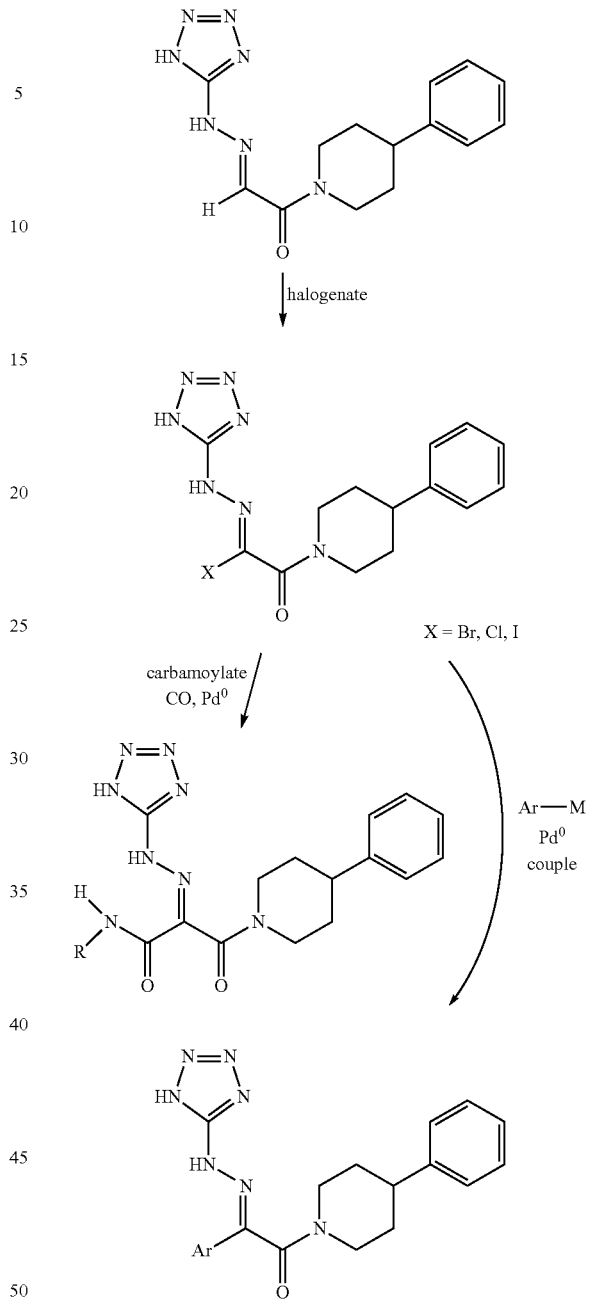

A method for introducing complex substitutions at the $R^{10}$ position is shown in Scheme 6. The known hydrazone-acid could be converted to the amide and halogenated electrophilically in the position alpha to the carbonyl. The resulting halogen should be amenable to carbonylation, or to coupling with various metallated aryl and alkyl synthons under the influence of transition metal (e.g. palladium 0) catalysis.

Scheme 6

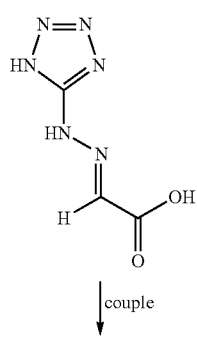

Scheme 7-9 describes a scaffold based on a chiral amino, 5-aminotetrazole. The schemes show how the carboxy terminus of a (S)-2-amino-3-(1H-indol-3-yl)propanoic acid derivative was elaborated with a tetrazole moiety, and linked using amide chemistry to a bulky bicycle at an appropriate distance from the chiral core to fill a targeted hydrophobic pocket.

The compound was then converted into a chiral aldehyde via the Meinwald amide using LAH. Other conditions could potentially be used. The aldehyde was combined with a benzyl-protected 5-amino tetrazole using reductive amination. De-BOC-ing the resulting synthon afforded a chiral amine which formed the core of this particular scaffold.

Scheme 7

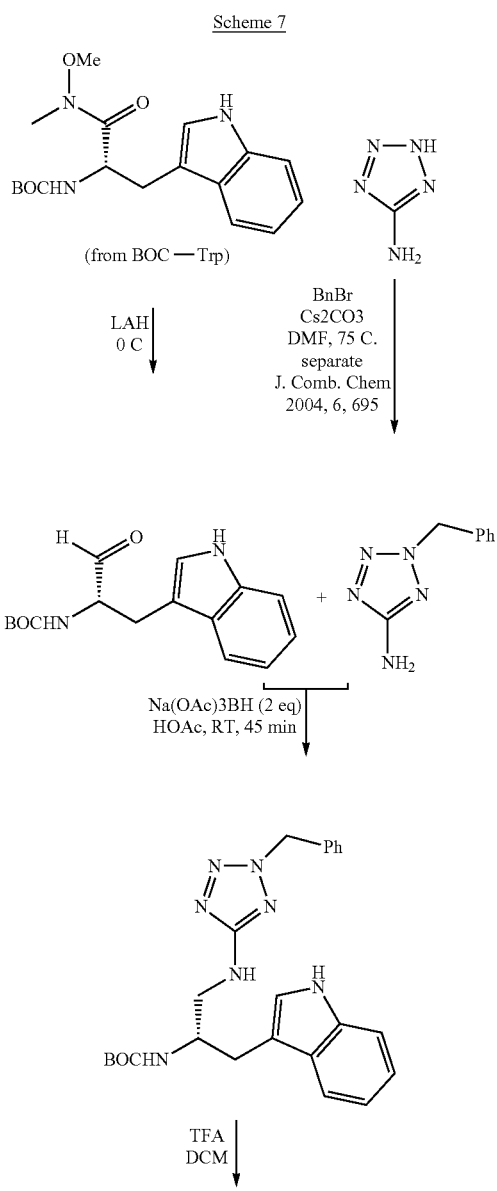

Scheme 8

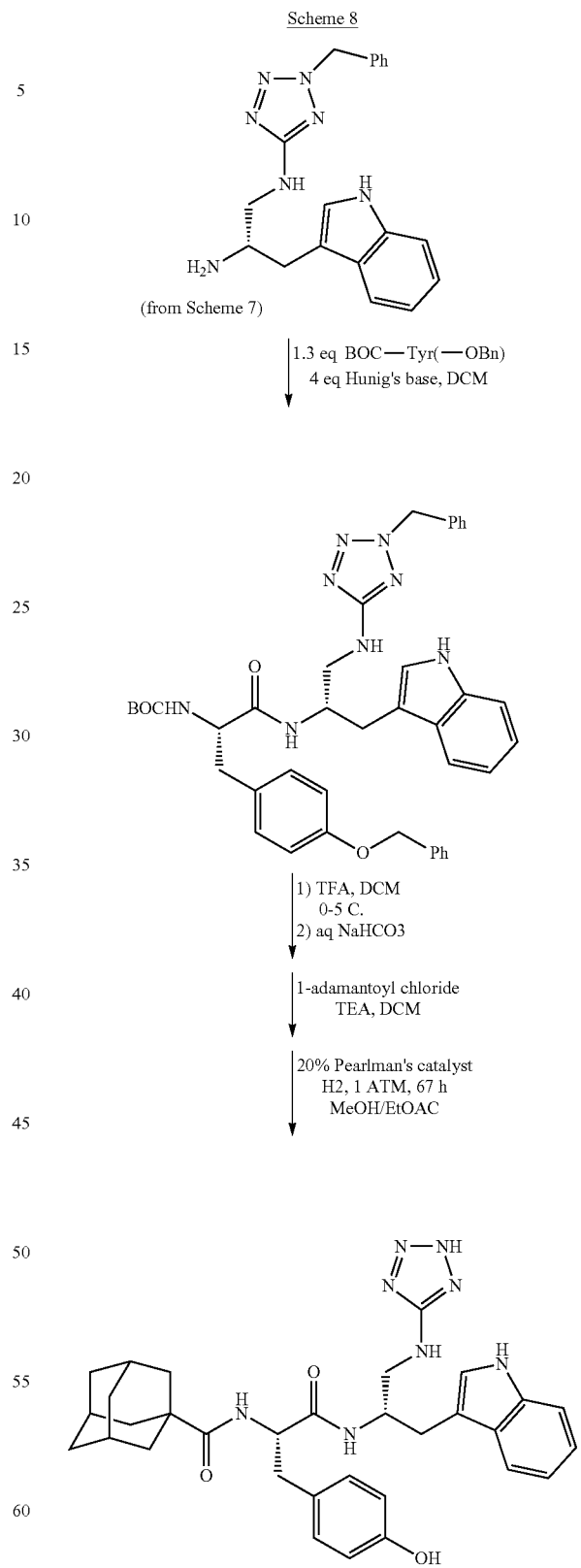

In scheme 8, the chiral subunit is elaborated with (S)-3-(4-(benzyloxy)phenyl)-2-((tert-butoxycarbonyl)amino)propanoic acid. The resulting piece is de-BOC'd and capped with 1-adamantoyl chloride. The two benzyl protecting groups are removed.

Alternately, one could debenzylate the chiral subunit (Scheme 9) and react with an adamantyl acrylate to create an olefinic variant of the desired scaffold.

Scheme 9

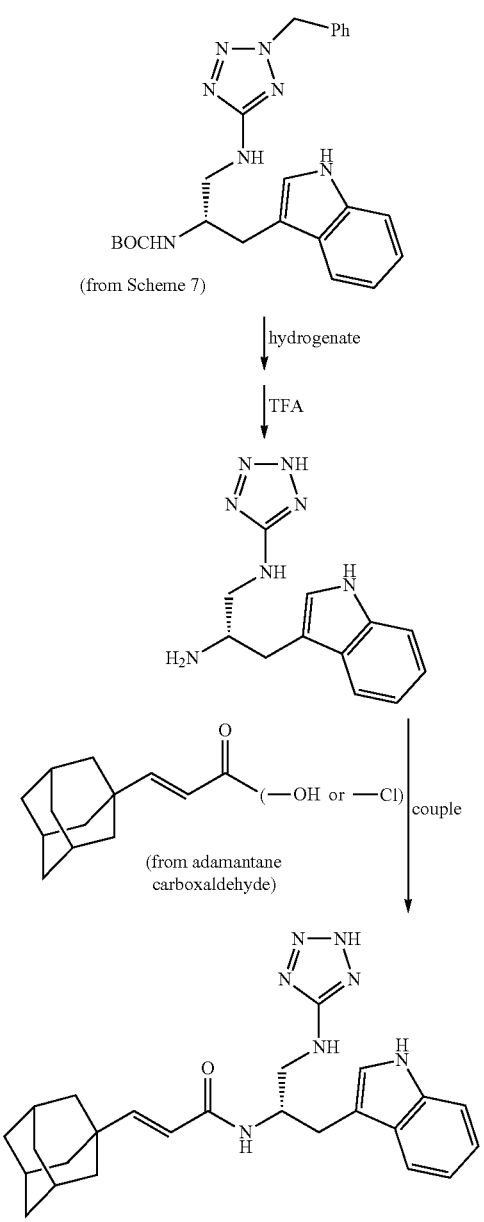

Another variation on this scaffold would be to use a 5 or 6 membered heterocycle to separate the bicyclic portion from the chiral amine. Preparation of a potential analog incorporating an oxadiazole spacer is depicted in Scheme 10:

Scheme 10

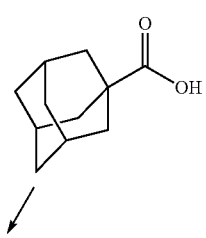

Adamantane carboxylic acid could be converted to an oxadiazole using a variety of literature methods and halogenated. The halogen could be displaced using the key chiral amine thermally; such displacements have been described in the literature (Ewing, W. R., et al. US 2013 0184284)

EXAMPLES

The present description is further illustrated by the following examples, which should not be construed as limiting in any way. The contents of all cited references (including literature references, issued patents, published patent applications as cited throughout this application) are hereby expressly incorporated by reference.

Example I

Cell Culture and Transfections

HepG2/shPCSK9 or HuH7/shPCSK9 cells (1) lacking endogenous PCSK9 were seeded at $1 \times 10^5$ cells/well in a 12 well microplate (Greiner Bio-One). These cells were then incubated for 4 h or overnight with 0.7 µg/ml of either V5-tagged PCSK9 or its gain-of-function PCSK9-D374Y pre-incubated, or not, for 4 h with each small molecule compound at 50 µM (or less if needed for the most active compounds). The cells were then lysed in 1×RIPA buffer (150 mM NaCl, 50 mM Tris-HCl, pH 8.0), containing 1% Nonidet P-40, 0.5% sodium deoxycholate, 0.1% SDS supplemented with 1× complete protease inhibitor mixture (Roche Applied Science), and analyzed by Western blot.

Example II

FACS Analysis

Cells, such as HepG2, HuH7, FL83B or a cell line transfected with a short-hairpin PCSK9 knockdown sequence such as HepG2/shPCSK9, HuH7/shPCSK9, FL83B/shPCSK9 will be incubated at 37° C. for 4 h, as described above, with PCSK9 pre-incubated with each of the exemplified small molecule compounds used at 50 μM (or less if needed for the most active compounds) plus a specimen that will be preincubated with a no-compound control. Benjannet et al., "Effects of the prosegment and pH on the activity of PCSK9: evidence for additional processing events" *J Biol Chem.* 285(52): 40965-40978 (2010).

The cells will be washed 3× with solution A (calcium/magnesium-free Dulbecco's PBS (Invitrogen) containing 0.5% bovine serum albumin (Sigma) and 1 g/liter glucose)). The cells will be incubated for 10 min at room temperature with 1× Versene solution (Invitrogen) which will then be followed by the addition of 5 ml of solution A. The cells will be incubated for 40 min in solution A containing a human LDLR mAb-C7 (1:100; Santa Cruz Biotechnology). Following washes, the cells will be incubated for 20 min in solution A containing a secondary antibody (Alexa Fluor 647 donkey anti-mouse antibody; 1:250; Molecular Probes).

Cells will then be suspended in PBS containing 0.2% of propidium iodide, the cells will be analyzed by FACS for both propidium iodide (dead cells) and LDLR in live cells with Alexa Fluor 647 using the FACS BD LSR (BD Biosciences). Cells incubated with small molecule compounds that are inhibitors of PCSK9 will be expected to show increased amounts of LDLR, relative to no compound specimens, and cells incubated with small molecule compounds that are activators of PCSK9 will be expected to show decreased amounts of LDLR relative to no compound specimens.

Example III

Cellular diI-LDL Uptake Assay

Cells, such as HepG2, HuH7, FL83B or a cell line transfected with a short-hairpin PCSK9 knockdown sequence such as HepG2/shPCSK9, HuH7/shPCSK9, FL83B/shPCSK9, were seeded at 2×10$^4$ cells/well in a 96-well plate and cultured at 37 deg C. in RPMI+10% FBS. After approximately 24 hours, the cell media was aspirated off and replaced with RPMI+3-5 mg/mL LPDS (Lipoprotein Deficient Serum, Millipore) media for further experimentation. Benjannet et al., "Effects of the prosegment and pH on the activity of PCSK9: evidence for additional processing events" *J Biol Chem.* 285(52): 40965-40978 (2010).

Small molecule compound activity was assessed by culturing cells with: i) no SRX compound/PCSK9 protein complex (control, Cnt); ii) PCSK9 protein; and iii) SRX compound/PCSK9 complex. Various permutations of these experimental conditions were also used, including: i) the addition of wild type PCSK9 (WT); ii) a mutant PCSK9 (e.g., D374Y mutant PCSK9, DY); iii) various SRX compounds and/or PCSK9 at the same concentration and/or combinations; iv) various SRX compounds and/or PCSK9 at different concentrations and/or combinations; v) the use of different cells, as mentioned above, with or without a transfected short-hairpin sequence; vi) a pre-incubation of the PCSK9 and SRX compound (e.g., 1, hour, 2 hours, 3 hours, 4 hours etc.); vii) various temperatures including, but not limited to, body temperature (e.g., 37° C.), supraphysiologic temperature (e.g., 39° C.); and viii) with/without agitation (e.g., shaker or gentle periodic vortexing).

Cells were cultured using one of the combinations of conditions described in the preceding paragraph for 16 hours. After 16 hours, a quantity of diI-LDL (Low density lipoprotein coupled with 1,1'-dioctadecyl-3,3,3',3'-tetramethylindocarbocyanine perchlorate) needed to bring the media concentration to 5 ug/mL of diI-LDL was added to the culture well and cells continued to be cultured under these new conditions for 4 additional hours. At the end of the 4-hour incubation period (20 total hours of cell culture), the cellular uptake was halted with the addition of 4% formaldehyde in 10 uM Hoechst 33342 in a solvent such as deionized autoclaved water or PBS, and specimens were incubated at 20° C. for 20 minutes. Cell specimens were rinsed twice with PBS and then fluorescence measured with excitation at 360 nm and emission detected at 460 nm to measure DNA content. Cell specimens were then be incubated with a 0.1% SDS in a 0.1 N NaOH solution while being shaken for 10 minutes. Fluorescence of the diI-LDL in the specimens were quantified using excitation at 530 nm and resulting emission at 580 nm.

Fluorescence measurements of diI-LDLR were normalized to estimated cell numbers, determined from the Hoechst fluorescence. Data was analyzed for the different experimental conditions and reported as percentage relative fluorescence units (RFU) of the Cnt specimen. Percent inhibition was calculated as the difference in RFU of a compound exposed specimen to the RFU of PCSK9-no compound, divided by the RFU difference in RFU of Cnt specimen minus PCSK9-no compound RFU; also expressed as [(SRX:RFU)−(PCSK9-no compound:RFU)]/[(Cnt:RFU)−(PCSK9-no compound:RFU)]×100%.

Example IV

Direct Binding Measurement

Direct binding was measured using backscatter interferometry, which has been previously described in "Interferometric detection system and method" (EP 1210581), "Free solution measurement of molecular interactions by backscattering interferometry" (WO 2009039466), "Temperature-stable interferometer" (WO 2009076372), and "Improved event detection for back-scattering interferometry" (WO 2013158300); which are incorporated herein by reference. For example, using a 6-point binding curve, SRX200 was measured to bind to recombinant human PCSK9 with a measured Kd of 24 nM±8 nM, with an r$^2$ of 0.86.

Example V

SRX75 Synthesis

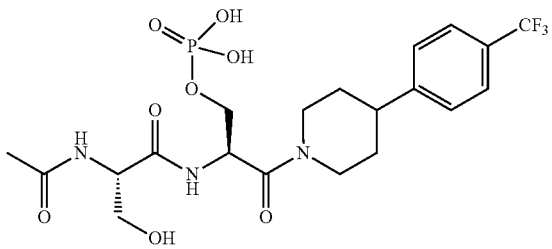 [SMILES: CC(=O)N[C@@H](CO)C(=O)N[C@@H](COP(=O)(O)O)C(=O)N1CCC(c2ccc(C(F)(F)F)cc2)CC1]

SRX75: (S)-2-((S)-2-acetamido-3-hydroxypropanamido)-3-oxo-3-(4-(4-(trifluoromethyl)phenyl)piperidin-1-yl)propyl Dihydrogen Phosphate (9H-fluoren-9-yl)methyl ((2S)-1-hydroxy-3-(((benzyloxy)(hydroxy)phosphoryl)oxy)-1-oxopropan-2-yl)carbamate [158171-14-3] was attached to 2-chlorotrityl resin. The Fmoc protecting group was removed. The N-terminus was reacted with (S)-2-acetamido-3-(tert-butoxy)propanoic acid [77285-09-7] using uronium based amide coupling reagents, and the resulting (S)-2-((S)-2-acetamido-3-(tert-butoxy)propanamido)-3-hydroxy-3-oxopropyl benzyl hydrogen phosphate was cleaved from the resin base by reaction using 1% TFA in DCM 2×1 hr.

(S)-2-((S)-2-acetamido-3-(tert-butoxy)propanamido)-3-hydroxy-3-oxopropyl benzyl hydrogen phosphate was then condensed with 4-(4-trifluoromethylphenyl)-piperidine HCl. Separately, 1 molar equivalent of each compound was solubilized in NMP. 1 equivalent of pybop and 3 equivalents NMM were added to the (S)-2-((S)-2-acetamido-3-(tert-butoxy)propanamido)-3-hydroxy-3-oxopropyl benzyl hydrogen phosphate solution, followed by the 4-(4-trifluoromethylphenyl)-piperidine HCl solution. The reaction was allowed to stir overnight, then another equivalent of 4-(4-trifluoromethylphenyl)-piperidine HCl in NMP was added to the reaction solution, along with another equivalent of pybop, and 2 equivalents of NMM. The progress of the reaction was followed by MS analysis, and deemed complete when no starting material could be seen.

Protecting groups were removed from the compound by cleaving for 2 hours using a cocktail of 93% TFA, 2.5% water, 2.5% ethanedithiol, 1% triethylsilane, and 1% thioanisole. A 10:1 ratio of cleavage cocktail to reaction solution was used. After 2 hours, the reaction was diluted with water, frozen and lyophilized overnight.

Post lyophilization, the compound was purified by normal phase silica chromatography, running an ethyl acetate/methanol gradient. After collecting and drying the appropriate fractions, the compound was purified by means of reverse phase HPLC, running an H2O/acetonitrile gradient on a C18 column. Fractions were lyophilized, affording (S)-2-((S)-2-acetamido-3-hydroxypropanamido)-3-oxo-3-(4-(4-(trifluoromethyl)phenyl)piperidin-1-yl)propyl dihydrogen phosphate.

$^1$H NMR (400 MHz, CD$_3$OD-d$_6$) δ 7.60 (d, 2H), 7.47 (m, 2H), 5.24 (m, 1H), 4.69 (m, 1H), 4.48 (m, 1H), 4.27 (m, 1H), 4.18 (m, 2H), 3.80 (m, 2H), 3.28 (m, 1H), 2.97 (m, 1H), 2.83 (m, 1H), 2.05 (s, 3H), 1.91-1.61 (m, 4H).

Example VI

SRX206 Synthesis

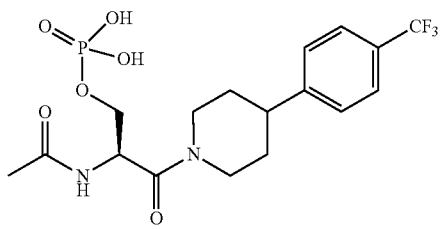 [SMILES: CC(=O)N[C@@H](COP(=O)(O)O)C(=O)N1CCC(c2ccc(C(F)(F)F)cc2)CC1]

SRX206: [(3 S)-3-Acetamido-4-oxo-4-{4-[4-(trifluoromethyl)phenyl]-piperidin-1-yl}butyl]phosphonic Acid Step 1: Preparation of diethyl [(3S)-3-{[(benzyloxy)carbonyl]amino}-4-oxo-4-{4-[4-(trifluoromethyl)phenyl]piperidin-1-yl}butyl]phosphonate A stirred solution of (2S)-2-{[(benzyloxy)carbonyl]amino}-4-(diethoxyphosphoryl)butanoic acid (Caroff, et al, U.S. Pat. Nos. 8,518,912, 2,013,960 mg, 2.57 mmol) in THF (5 mL)/methylene chloride (20 mL) under nitrogen was sequentially treated with N,N-diisopropylethylamine (1.79 mL, 10.3 mmol), 1-hydroxybenzotriazole hydrate (472 mg, 3.08 mmol) and N-(3-dimethylaminopropyl)-N'-ethylcarbodiimide hydrochloride (592 mg, 3.08 mmol), and the mixture was stirred for 10 min. 4-[4-(Trifluoromethyl)phenyl] piperidine hydrochloride (717 mg, 2.70 mmol) was added, and the resulting mixture was stirred at room temperature overnight. At 18 h, the mixture was diluted with methylene chloride (40 mL), washed with saturated aqueous NaHCO$_3$ (30 mL) and ½-saturated brine (25 mL), dried over Na$_2$SO$_4$ and concentrated and dried under reduced pressure. Purification by silica gel chromatography (40 g, 50-100% EtOAc/hexanes, then 5% EtOH/EtOAc eluent) gave 1.10 g (73%) of the title compound as a colorless gum. MS (ESI+) for C$_{28}$H$_{36}$F$_3$N$_2$O$_6$P m/z 585.7 (M+H)$^+$; HPLC ret time: 4.35 min (>99.0% purity).

Step 2: Preparation of diethyl [(3 S)-3-amino-4-oxo-4-{4-[4-(trifluoromethyl)phenyl]-piperidin-1-yl}butyl]phosphonate A solution of diethyl [(3 S)-3-{[(benzyloxy)carbonyl]amino}-4-oxo-4-{4-[4-(trifluoromethyl)phenyl]piperidin-1-yl}butyl]phosphonate (Step 1, 470 mg, 0.80 mmol) in MeOH (8 mL) under nitrogen was treated with 10% Pd/C (61% water wet Degussa type, 43 mg, 0.016 mmol). The mixture was evacuated and backfilled with nitrogen several times and then with hydrogen and stirred under a hydrogen atmosphere (double balloon) for 3 h. The catalyst was removed by filtration through solka flok, and the filtrate was concentrated and dried under reduced pressure to give 356 mg (98%) of the title compound as a colorless gum. MS (ESI+) for C$_{20}$H$_{30}$F$_3$N$_2$O$_4$P m/z 451.8 (M+H)$^+$; HPLC ret time: 3.40 min (>99.0% purity).

Step 3: Preparation of diethyl [(3S)-3-acetamido-4-oxo-4-{4-[4-(trifluoromethyl)-phenyl]piperidin-1-yl}butyl]phosphonate A stirred solution of diethyl [(3 S)-3-amino-4-oxo-4-{4-[4-(trifluoromethyl)phenyl]piperidin-1-yl}butyl]phosphonate (Step 2, 350 mg, 0.777 mmol) in methylene chloride (7.8 mL) under nitrogen was treated dropwise with pyridine (126 µL, 1.55 mmol) followed by acetic anhydride (88.0 µL, 0.932 mmol), and the resulting colorless, homogeneous mixture was stirred at room temperature overnight. At 20 h, the reaction mixture was diluted with methylene chloride (20 mL), washed with saturated aqueous NaHCO$_3$ (10 mL), water (10 mL) and brine (5 mL), dried over Na$_2$SO$_4$ and concentrated and dried under reduced pressure. Purification by radial chromatography [2000 micron silica gel rotor; 0-15% EtOH/EtOAc eluent] gave 385 mg (100%) of the title compound as a colorless viscous oil. MS (ESI+) for C$_{22}$H$_{32}$F$_3$N$_2$O$_5$P m/z 493.6 (M+H)$^+$; HPLC ret time: 3.73 min (>99.0% purity).

Step 4: Preparation of [(3S)-3-acetamido-4-oxo-4-{4-[4-(trifluoromethyl)phenyl]-piperidin-1-yl}butyl] phosphonic Acid A stirred solution of diethyl [(3 S)-3-acetamido-4-oxo-4-{4-[4-(trifluoromethyl)phenyl]piperidin-1-yl}butyl]phosphonate (Step 3, 290 mg, 0.589 mmol) in dry acetonitrile (2 mL) under nitrogen was cooled in an ice-water bath and treated with bromotrimethylsilane (1.6 mL, 12 mmol) dropwise.

The resulting homogeneous mixture was stirred with cooling for 30 min, and then the cooling bath was removed and the reaction was allowed to stir at room temperature. At 3.25 h, the mixture was cooled in an ice-water bath, treated dropwise with water (5 mL) and stirred at room temperature for 30 min. The mixture was diluted with additional water (3 mL) and extracted with methylene chloride (5×20 mL), and the combined organic phase was dried over $Na_2SO_4$ and concentrated under reduced pressure. Purification by preparative HPLC on a CombiFlash Rf system [150 g C18Aq Gold column; elution with a gradient of 0-50% acetonitrile (0.07% TFA)/water (0.1% TFA)] and lyophilization of product fractions afforded 187 mg (73%) of the title compound as a white amorphous solid.

$^1$H NMR (400 MHz, DMSO-$d_6$) δ 8.24 (d, J=8.4 Hz, ~0.5H), 8.16 (d, J=8.0 Hz, ~0.5H), 7.67 (m, 2H), 7.48 (m, 2H), 4.82 (m, 1H), 4.54 (bd, J=12 Hz, 1H), 4.11 (bt, J=14 Hz, 1H), 3.11 (m, 1H), 2.94 (m, 1H), 2.67 (bq, J=12 Hz, 1H), 1.858/1.851 (two s, 3H), 1.85-1.40 (m, 8H); MS (ESI–) for $C_{18}H_{24}F_3N_2O_5P$ m/z 435.2 (M–H)$^-$; HPLC ret time: 3.01 min (99.0% purity).

Example VII

SRX201 Synthesis

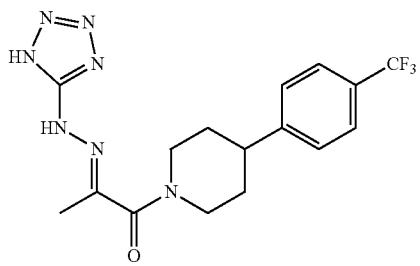 [SMILES: C/C(=N\Nc1nnn[nH]1)C(=O)N1CCC(c2ccc(C(F)(F)F)cc2)CC1]

SRX201: (2E)-1-Oxo-1-{4-[4-(trifluoromethyl)phenyl]piperidin-1-yl}acetone 1H-tetrazol-5-ylhydrazone Step 1: Preparation of (2E)-2-(1H-tetrazol-5-ylhydrazono)propanoic Acid A vigorously stirred solution of 5-hydrazino-1H-tetrazole hydrochloride (278 mg, 2.04 mmol) in water (3 mL) was treated quickly with a solution of sodium 2-oxopropanoate (224 mg, 2.04 mmol) in water (2 mL), and the resulting off-white slurry was stirred at room temperature for 4 h. The solids were isolated by filtration, washed with water (3×0.5 mL) and dried under high vacuum overnight to give 306 mg (88%) of the title compound as an off-white solid. 1H NMR (400 MHz, DMSO-d6) 15.55 (bs, 0.5-1H), 12.00 (bs, ~1H), 11.64 (s, ~1H), 2.08 (s, 3H); MS (ESI–) for C4H6N6O2 m/z 169.1 (M–H)–.

Step 2: Preparation of (2E)-1-oxo-1-{4-[4-(trifluoromethyl)phenyl]piperidin-1-yl}acetone 1H-tetrazol-5-ylhydrazone A stirred solution of (2E)-2-(1H-tetrazol-5-ylhydrazono) propanoic acid (Step 1, 94 mg, 0.56 mmol) and N,N,N',N'-tetramethyl-O-(7-azabenzotriazol-1-yl)uronium hexafluorophosphate (290 mg, 0.762 mmol) in DMF (2.7 mL) under nitrogen was treated with N,N-diisopropylethylamine (354 L, 2.03 mmol) to give a red-orange homogeneous mixture, stirred for 10 min and treated with 4-[4-(trifluoromethyl) phenyl]piperidine hydrochloride (135 mg, 0.508 mmol). The resulting amber homogeneous mixture was stirred at room temperature and monitored by HPLC. At ~19 h, the mixture was diluted with EtOAc (30 mL), washed with aqueous citric acid (0.5 M, 4×20 mL) and brine (2×10 mL), dried over MgSO4 and concentrated under reduced pressure to give the crude product which was split in two batches and purified by preparative HPLC [CombiFlash Rf system; 30 g C18Aq Gold column; elution with a gradient of 0-80% methanol (0.07% TFA)/water (0.1% TFA)]. Product fractions (~95% purity) were pooled and concentrated, the aqueous residue was extracted with EtOAc (35 mL), and the organic phase was dried over MgSO4 and concentrated under reduced pressure. Repurification by preparative HPLC [CombiFlash Rf system; 30 g C18Aq Gold column; elution with a gradient of 10-50% acetonitrile (0.07% TFA)/water (0.1% TFA)] and lyophilization of product fractions afforded 49 mg (25%) of the title compound as a white flocculent solid.

$^1$H NMR (300 MHz, DMSO-d6) 15.21 (bs, 0.2-1H), 10.89 (s, 1H), 7.68 (d, J=8.4 Hz, 2H), 7.52 (d, J=8.1 Hz, 2H), 4.53 (bd, J=13 Hz, 1H), 3.97 (bd, J=13 Hz, 1H), 3.21 (m, 1H), 2.95 (m, 1H), 2.80 (m, 1H), 2.10 (s, 3H), 1.91-1.50 (m, 4H); MS (ESI+) for C16H18F3N7O m/z 382.1 (M+H)+; HPLC ret time: 3.58 min (98.0% purity). Analytical HPLC conditions: Agilent 1100 HPLC. Zorbax Eclipse XDB-C18 50×4.6 mm column. Solvent A—Water (0.1% TFA); Solvent B—Acetonitrile (0.07% TFA). Flow rate—1.50 mL/min. Gradient—5 min 95% A to 90% B, 1 min hold, then recycle to 95% A over 1 min. UV detection @ 214 and 254 nm.

Example VIII

SRX205 Synthesis

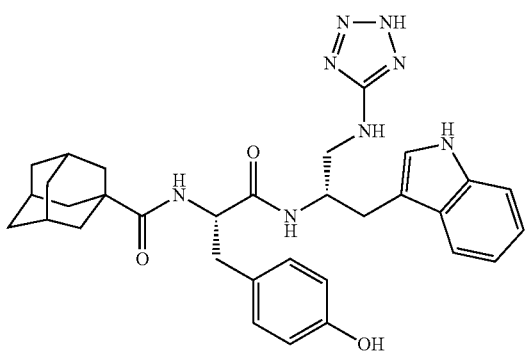

SRX205

5-Aminotetrazole was protected by benzyl in the 2-position (J. Comb. Chem., 2004, 6, 695) and reacted (Na(OAc)3BH, HOAc) with the aldehyde derived from tert-butyl (S)-(1-hydroxy-3-(1H-indol-3-yl)-1-oxopropan-2-yl)carbamate. The resulting chiral subunit was de-BOC'ed (TFA/DCM) and coupled (EDC, Hunig's base) with (S)-3-(4-(benzyloxy) phenyl)-2-((tert-butoxycarbonyl)amino)propanoic acid. This, again, was de-BOC'ed and reacted with 1-adamantoyl chloride (TEA). Removal of both benzyl protecting groups was accomplished using 20% Pearlman's catalyst over 67 hours under a hydrogen balloon. MS (ESI–) for C32H38N8O3 m/z 581.1 (M–H),

We claim:

1. A method, comprising:
   a) providing;
      i) a PCSK9 protein, wherein said protein comprises a binding site that induces allosteric modulation and a low density lipoprotein receptor binding site;
      ii) a pharmaceutical formulation comprising a small molecule ligand capable of binding said binding site, wherein said small molecule ligand is an allosteric inhibitor ligand;
      iii) a plurality of hepatocyte cells comprising a population of low density lipoprotein receptors; and
      iv) low density lipoproteins;
   b) binding said small molecule ligand to said binding site, wherein said small molecule ligand induces a conformational shift of said protein; and
   c) modulating said population of said low density lipoprotein receptors by said conformational shift.

2. The method of claim 1, wherein said pharmaceutical formulation further comprises a first pharmaceutical drug.

3. The method of claim 2, wherein said first pharmaceutical drug comprises a cardiovascular drug.

4. The method of claim 3, wherein said cardiovascular drug is selected from the group consisting of a statin and ezetimibe.

5. The method of claim 1, wherein said small molecule ligand is an organic chemical compound less than 800 Da.

6. The method of claim 1, wherein said PCSK9 protein allosteric inhibitor ligand increases the population of low density lipoprotein receptors measurable on the cell surface of said plurality of hepatocytes.

7. The method of claim 1, wherein said PCSK9 protein allosteric inhibitor ligand decreases the affinity of the PCSK9 protein's low density lipoprotein receptor binding site for the low density lipoprotein receptor on said plurality of hepatocytes.

8. The method of claim 1, wherein said allosteric inhibitor ligand increases the internalization of said low density lipoproteins by said hepatocytes.

9. A method, comprising binding a small molecule compound to a PCSK9 protein allosteric modulation site, to increase the population of low density lipoprotein receptors measurable on the cell surface of a plurality of hepatocytes.

10. The method of claim 9, wherein said small molecule compound increases the internalization of low density lipoproteins by said hepatocytes.

11. A method of administering to a subject a small molecule compound, the method comprising binding said small molecule compound to a PCSK9 protein allosteric binding site, wherein said subject has at least one symptom of cardiovascular disease under conditions such that said at least one symptom of a cardiovascular disease is reduced.

12. The method of claim 11, wherein said at least one symptom comprises elevated circulating low density lipoprotein.

13. The method of claim 11, wherein said at least one symptom is reduced between 10%-85%.

14. The method of claim 11, wherein said cardiovascular disease is selected from the group consisting of a coronary disease, hypertension, hypercholesterolemia and atherosclerosis.

15. The method of claim 11, wherein said administering comprises an effective dose of said small molecule compound.

16. The method of claim 11, wherein said small molecule compound is a pharmaceutical composition.

17. The method of claim 11, wherein said small molecule compound is an organic chemical compound less than 800 Da.

18. The method of claim 11, wherein said small molecule compound binds said PCSK9 protein with a binding affinity of less than 500 nM.

19. The method of claim 16, wherein said pharmaceutical composition is further combined with a second pharmaceutical compound.

20. The method of claim 11, wherein said small molecule compound is selected from the group consisting of SRX75, SRX76, SRX200, SRX201, SRX204, SRX205, SRX206, SRX207, SRX208, SRX209, SRX210, SRX211, SRX212, SRX213, SRX214, SRX215, SRX216, SRX217, SRX218, SRX219, SRX220, SRX221, SRX222, SRX223, SRX224, and SRX225.

* * * * *

SEQUENCE LISTING

<160> NUMBER OF SEQ ID NOS: 1

<210> SEQ ID NO 1
<211> LENGTH: 692
<212> TYPE: PRT
<213> ORGANISM: Homo sapiens

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
            85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
            130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365
```

```
Ile Gly Ala Ser Ser Asp Cys Ser Thr Cys Phe Val Ser Gln Ser Gly
    370             375                 380
Thr Ser Gln Ala Ala Ala His Val Ala Gly Ile Ala Ala Met Met Leu
385             390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
Gln Arg Val Leu Thr Pro Asn Leu Val Ala Ala Leu Pro Pro Ser Thr
            435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
                660                 665                 670
Thr Ala Val Ala Ile Cys Cys Arg Ser Arg His Leu Ala Gln Ala Ser
            675                 680                 685
Gln Glu Leu Gln
    690
```